United States Patent
Cox et al.

(10) Patent No.: US 7,258,697 B1
(45) Date of Patent: Aug. 21, 2007

(54) STENT WITH ANCHORS TO PREVENT VULNERABLE PLAQUE RUPTURE DURING DEPLOYMENT

(75) Inventors: Daniel L. Cox, Palo Alto, CA (US); Christopher Feezor, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 645 days.

(21) Appl. No.: 10/744,115

(22) Filed: Dec. 22, 2003

(51) Int. Cl.
*A61F 2/06* (2006.01)
(52) U.S. Cl. .................... 623/1.16; 623/1.14; 623/1.15
(58) Field of Classification Search ............... 623/1.12, 623/1.14–1.16, 1.32, 1.28, 1.1, 1.11
See application file for complete search history.

(56) References Cited

U.S. PATENT DOCUMENTS

| | | | |
|---|---|---|---|
| 2,701,559 A | 2/1955 | Cooper | |
| 3,105,492 A | 10/1963 | Jeckel | |
| 3,657,744 A | 4/1972 | Ersek | |
| 3,868,956 A | 3/1975 | Alfidi et al. | |
| 3,993,078 A | 11/1976 | Bergentz et al. | |
| 4,130,904 A | 12/1978 | Whalen | |
| 4,140,126 A | 2/1979 | Choudhury | |
| 4,159,719 A | 7/1979 | Haerr | |
| 4,323,071 A | 4/1982 | Simpson | |
| 4,387,952 A | 6/1983 | Slusher | |
| 4,503,569 A | 3/1985 | Dotter | |
| 4,504,354 A | 3/1985 | George et al. | |
| 4,512,338 A | 4/1985 | Balko et al. | |
| 4,516,972 A | 5/1985 | Samson | |
| 4,531,933 A | 7/1985 | Norton et al. | |
| 4,553,545 A | 11/1985 | Maass et al. | |
| 4,560,374 A | 12/1985 | Hammerslag | |
| 4,580,568 A | 4/1986 | Gianturco | |
| 4,616,652 A | 10/1986 | Simpson | |
| 4,619,246 A | 10/1986 | Molgaard-Nielsen et al. | |

(Continued)

FOREIGN PATENT DOCUMENTS

DE 3640745 A1 6/1987

(Continued)

OTHER PUBLICATIONS

U.S. Application No. 10/322,350, filed Dec. 18, 2002, Cox et al.

(Continued)

*Primary Examiner*—Anhtuan T. Nguyen
*Assistant Examiner*—Pavitra Kotini
(74) *Attorney, Agent, or Firm*—Paul Y. Feng; Fulwider Patton LLP

(57) ABSTRACT

A stent for implantation in a body lumen for protecting from rupture a fibrous cap in order to treat vulnerable plaque. One embodiment of the stent achieves staged expansion through stronger and weaker circumferential regions, and includes optional anchors positioned at the circumferential transition between the stronger and weaker regions. During the first stage expansion, the weaker region expands moving the anchors laterally apart. The anchors straddle the fibrous cap and embed into the vessel wall. The second stage expansion of the stent exerts gentler stresses by the weaker region against the fibrous cap while the stronger region exerts greater stresses on the remainder of the vessel wall to open the vessel.

20 Claims, 12 Drawing Sheets

U.S. PATENT DOCUMENTS

| | | |
|---|---|---|
| 4,649,922 A | 3/1987 | Wiktor |
| 4,650,466 A | 3/1987 | Luther |
| 4,655,771 A | 4/1987 | Wallsten |
| 4,665,918 A | 5/1987 | Garza et al. |
| 4,681,110 A | 7/1987 | Wiktor |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,776,337 A | 10/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,479 A | 5/1990 | Grayzel |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silvestrini |
| 5,242,394 A | 9/1993 | Tremulis |
| 5,242,399 A | 9/1993 | Lau et al. |
| 5,242,452 A | 9/1993 | Inoue |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,344,426 A | 9/1994 | Lau et al. |
| 5,354,308 A | 10/1994 | Simon et al. |
| 5,356,433 A | 10/1994 | Rowland et al. |
| 5,360,401 A | 11/1994 | Turnland et al. |
| 5,368,566 A | 11/1994 | Crocker |
| 5,372,600 A | 12/1994 | Beyar et al. |
| 5,378,239 A | 1/1995 | Termin et al. |
| 5,383,892 A | 1/1995 | Cardon et al. |
| 5,397,355 A * | 3/1995 | Marin et al. .................. 623/1.2 |
| 5,405,378 A | 4/1995 | Strecker |
| 5,421,955 A | 6/1995 | Lau et al. |
| 5,423,745 A | 6/1995 | Todd et al. |
| 5,423,885 A | 6/1995 | Williams |
| 5,445,646 A | 8/1995 | Euteneuer et al. |
| 5,449,373 A | 9/1995 | Pinchasik et al. |
| 5,456,694 A | 10/1995 | Marin et al. |
| 5,458,615 A | 10/1995 | Klemm et al. |
| 5,476,476 A | 12/1995 | Hillstead |
| 5,484,449 A | 1/1996 | Amundson et al. |
| 5,507,768 A | 4/1996 | Lau et al. |
| 5,514,154 A * | 5/1996 | Lau et al. .................. 623/1.15 |
| 5,545,132 A | 8/1996 | Fagan et al. |
| 5,571,135 A | 11/1996 | Fraser et al. |
| 5,591,223 A | 1/1997 | Lock et al. |
| 5,603,721 A | 2/1997 | Lau et al. |
| 5,609,628 A | 3/1997 | Keranen |
| 5,626,604 A | 5/1997 | Cottone, Jr. |
| 5,653,690 A | 8/1997 | Booth et al. |
| 5,653,691 A | 8/1997 | Rupp et al. |
| 5,653,727 A | 8/1997 | Wiktor |
| 5,690,644 A | 11/1997 | Yurek et al. |
| 5,716,396 A | 2/1998 | Williams, Jr. |
| 5,720,726 A | 2/1998 | Marcadis et al. |
| 5,733,303 A | 3/1998 | Israel et al. |
| 5,733,325 A | 3/1998 | Robinson et al. |

| | | | |
|---|---|---|---|
| 5,735,893 A | 4/1998 | Lau et al. | |
| 5,782,855 A | 7/1998 | Lau et al. | |
| 5,800,521 A | 9/1998 | Orth | |
| 5,810,871 A | 9/1998 | Tuckey et al. | |
| 5,817,152 A | 10/1998 | Birdsall et al. | |
| 5,830,217 A | 11/1998 | Ryan | |
| 5,836,965 A | 11/1998 | Jendersee et al. | |
| 5,876,419 A | 3/1999 | Carpenter et al. | |
| 5,893,852 A | 4/1999 | Morales | |
| 5,902,332 A | 5/1999 | Schatz | |
| 5,924,997 A | 7/1999 | Campbell | |
| 5,935,135 A * | 8/1999 | Bramfitt et al. | 623/1.11 |
| 5,951,599 A | 9/1999 | McCrory | |
| 5,984,964 A | 11/1999 | Roberts et al. | |
| 5,997,468 A | 12/1999 | Wolff et al. | |
| 6,027,526 A * | 2/2000 | Limon et al. | 623/1.15 |
| 6,030,413 A | 2/2000 | Lazarus | |
| 6,066,168 A | 5/2000 | Lau et al. | |
| 6,146,358 A | 11/2000 | Rowe | |
| 6,162,244 A * | 12/2000 | Braun et al. | 623/1.12 |
| 6,231,597 B1 | 5/2001 | Deem et al. | |
| 6,245,026 B1 | 6/2001 | Campbell et al. | |
| 6,261,305 B1 | 7/2001 | Marotta et al. | |
| 6,380,457 B1 | 4/2002 | Yurek et al. | |
| 6,423,090 B1 | 7/2002 | Hancock | |
| 6,450,971 B1 | 9/2002 | Andrus et al. | |
| 6,451,044 B1 | 9/2002 | Naghavi et al. | |
| 6,602,282 B1 * | 8/2003 | Yan | 623/1.15 |
| 6,755,855 B2 | 6/2004 | Yurek et al. | |
| 2001/0047138 A1 | 11/2001 | Kokate et al. | |
| 2002/0009535 A1 | 1/2002 | Michal et al. | |
| 2002/0062147 A1 | 5/2002 | Yang | |
| 2002/0077564 A1 | 6/2002 | Campbell et al. | |
| 2002/0082515 A1 | 6/2002 | Campbell et al. | |
| 2002/0091436 A1 | 7/2002 | Phelps et al. | |
| 2002/0099406 A1 | 7/2002 | St. Germain | |
| 2002/0151924 A1 * | 10/2002 | Shiber | 606/194 |
| 2002/0198592 A1 | 12/2002 | Wallace et al. | |
| 2003/0229370 A1 * | 12/2003 | Miller | 606/159 |

FOREIGN PATENT DOCUMENTS

| | | |
|---|---|---|
| DE | 3823060 A1 | 1/1989 |
| EP | 0 062 300 A2 | 10/1982 |
| EP | 0 221 570 A2 | 5/1987 |
| EP | 0 338 816 A2 | 10/1989 |
| EP | 0 361 192 A3 | 4/1990 |
| EP | 0 364 787 A1 | 4/1990 |
| EP | 0 372 789 A3 | 6/1990 |
| EP | 0 380 668 A1 | 8/1990 |
| EP | 0 407 951 A3 | 1/1991 |
| EP | 9 408 245 A1 | 1/1991 |
| EP | 0 421 729 A2 | 4/1991 |
| EP | 0 423 916 A1 | 4/1991 |
| EP | 0 428 479 A1 | 5/1991 |
| EP | 0 517 075 B1 | 12/1992 |
| EP | 0 540 290 A2 | 5/1993 |
| EP | 0 541 443 A1 | 5/1993 |
| EP | 0 807 424 A2 | 11/1997 |
| FR | 2 677 872 | 12/1992 |
| GB | 2 070 490 A | 9/1981 |
| GB | 2 135 585 A | 11/1983 |
| JP | 58-501458 | 9/1983 |
| JP | 62-213762 | 9/1987 |
| JP | 62-231657 | 10/1987 |
| JP | 62-235496 A | 10/1987 |
| JP | 63-214264 | 9/1988 |
| JP | 63-246178 | 10/1988 |
| JP | 64-83685 | 3/1989 |
| JP | 01083685 A | 3/1989 |
| JP | 1-299550 | 12/1989 |
| JP | 2-174859 | 7/1990 |
| JP | 2 255157 | 10/1990 |
| JP | 03009745 A | 1/1991 |
| JP | 03009746 A | 1/1991 |
| JP | 3-57465 | 3/1991 |
| JP | 3-151983 | 6/1991 |
| JP | 4-25755 | 2/1992 |
| WO | WO89/08433 | 9/1989 |
| WO | WO91/07139 | 5/1991 |
| WO | WO92/06734 | 4/1992 |
| WO | WO92/09246 | 6/1992 |
| WO | WO89/01798 | 11/1997 |

OTHER PUBLICATIONS

Dotter, Charles T. *Transluminally Placed Coilspring Endarterial Tube Grafts, Investigative Radiology*, pp. 329-332, Sep./Oct. 1969.

Dotter, Charles T., *Transluminal Expandable Nitinol Coil Stens Grafting: Preliminary Report, Radiology Journal*, pp. 259-260, Apr. 1983.

Cragg et al., *Non-Surgical Placement of Arterial Endoprostheses: A New Technique Using Nitinol Wire, Radiology Journal*, pp. 261-263, Apr. 1983.

Maass, et al., *Radiological Follow-Up of Transluminally Inserted Vascular Endoprostheses: An Experimental Study Using Expanding Spirals, Radiology Journal*, pp. 659-663, 1984.

C.R. Bard, *PE Plus Peripheral Balloon Dilation Catheter*, C.R. Bard, Inc., Aug. 1985.

Wright, et al., *Percutaneous Endovascular Stents: An Experimental Evaluation, Radiology Journal*, pp. 69-72, 1985.

Palmaz et al., *Expandable Intraluminal Graft: A Preliminary Study, Radiology Journal*, pp. 73-77, 1985.

Duprat et al., *Flexible Balloon-Expanded Stent for Small Vessels*, Radiology Journal, pp. 276-278 (1987).

Yoshioka et al., *Self-Expanding Endovascular Graft*: An Experimental Study in Dogs, *American Journal of Roentgeriology*, pp. 673-676, vol. 151, Oct. 1988.

Rosch, Jr., M.D. et al., *Transjugular Intrahepatic Portacaval Shunt: An Experimental Work*, The American Journal of Surgery, pp. 588-592, vol. 121, May 1971.

70th *Scientific Assembly and Annual Meeting: Scientific Program*, Radiology, Washington, D.C., Nov. 25-30, 1984, special Edition, vol. 153(P).

Chamsangavej, D., M.D. et al., *Endovascular Stent for Use in Aortic Dissection: An In Vitro Experiment, Radiology*, pp. 323-324, vol. 157, No. 2, Nov. 1985.

72nd *Scientific Assembly and Annual Meeting: RSNA Scientific Program*, Radiology, Chicago: Nov. 30-Dec 5, 1986, Special Edition, vol. 161(P).

Wallace, Michael J., et al., *Tracheobronchia Tree: Expandable Metallic Stents Used in Experimental and Clinical Applications (Work in Progress), Radiology*, pp. 309-312, vol. 158, Feb. 1986.

*Program: Day 2* (Nov. 18) The Radiological Society of North America, Radiology, Chicago: Nov. 30-Dec. 5, 1986, Special Edition, vol. 161(P).

Charnsangavej, Chusilp, M.D., et al., *Stenosis of the Vena Cava: Preliminary Assessment of Treatment with Expandable Metallic Stents, Radiology*, pp. 295-298, vol. 161, Nov. 1986.

Rosch, Josef, M.D., et al., *Experimental Intrahepatic Portacaval Anastomosis: Use of Expandable Gianturco Stents, Radiology*, pp. 481-485, vol. 162, Feb. 1987.

Rosch, Josef, M.D., et al., *Gianturco Expandable Stents in Experimental and Clinical Use*, paper presented at The Twelfth Annual Course on "Diagnostic Angiography and Interventional Radiology" Mar. 23-26, 1987 (Pittsburgh, Pennsylvania).

Finci, Leo, M.D., et al., *Percutaneous Transluminal Coronary Angioplasty of a Bifurcation Narrowing Using the Kissing Wire Monorail Balloon Technique. The American Journal of Cardiology*, pp. 375-376, vol. 60, Aug. 1987.

Lawrence, David D., Jr., M.D., et al., *Percutaneous Endovascular Graft: Experimental Evaluation, Radiology*, pp. 357-360, vol. 163, May 1987.

Rosch, Josef, M.D., et al., *Gianturco Expandable Wire Stents in the Treatment of Superior Vena Cava Syndrome Recurring after Maxinwm-Tolerance Radiation*, Cancer, pp. 1243-1246, vol. 60, Sep. 1987.

Bonzel, T., et al., *The Sliding Rail System (Monorail): Description of a New Technique for Intravascular Instrumentation and Its Application to Coronary Angloplasty*, Kardiologic, Supplement 6, pp. 119-122, 1987.

Rosch, Josef, M.D., et al., *Modified Gianturco Expandable Wire Stents in Experimental and Clinical Use*, Annales de Radiologie, pp. 100-103, vol. 31, No. 2, 1988.

Yoshioka et al., *Development and Clinical Application of Biliary Endoprosthesis Using Expandable Metallic Stents*, Japan Radiological Society, 1988, vol. 48, No. 9, pp. 1183-1185 (with translation).

Mirich, et al., *Percutaneously Placed Endovascular Grafts for Aoertic Aneurysms: Feasibility Study*, Radiology, 1989, part 2, pp. 1033-1037.

Furui, Shigeru, M.D., et al., *Hepatic Inferior Vena Cava Obstruction: Treament of Two Types with Gianturco Expandable Metallic Stents*, Radiology, pp. 665-670, Sep. 1990.

Kaltenbach, M., Prof. Dr., Abstracts, *Zeitschrift fur Kardiologie*, Apr. 3, 1991 (Germany only).

van der Geissen, Willem J., et al., *Coronary Stenting with a New, Radiopaque Balloon-Expandable Endoprosthesis in Pigs*, Circulation, vol. 83, No. 5, pp. 93-149, May 1991.

Strupp, G., et al., *Clinical and Angiographic Short and Medium Term Results after Coronary Stenting*, Zietschrift fur Kardiologie, Sep. 9, 1992 (German with English language summary).

Harrington, J.D., et al., *The Palmaz-Schatz Stent, Handbook of Cardiovascular Interventions/Vascular Internventions*, pp. 563-572 (undated).

Yoshioka, et al., *Self-Expanding Endovascular Graft: An Experiment Study In Dogs AJR*, vol. 151, pp. 673-676 1988.

Yoshioka, et al., *Development And Clinical Application of Biliary Endoprosthesis Using Expandable Metallic Stents.*, Japan Radiological Society, vol. 48, pp. 1183-1185 1988.

Richardson, *Influence of Plaque Configuration And Stress Distribution On Fissuring Of Coronary Atherosclerotic Plaques*, The Lancet, pp. 941-944, Oct. 1988.

Serruys, et al., *Morphologic Change In Coronary Artery Stenosis With The Medtronic Wiktor™ Stent: Initial Results From The Core Laboratory For Quantitative Angiography*, Catheterization and Cardiovascular Diagnosis, vol. 24, pp. 237-245 1991.

Loree, et al., *Effects of Fibrous Cap Thickness On Peak Circumferential Stress In Model Atherosclerotic Vessels*, Circulation Research, vol. 71, No. 4, pp. 850-858 1992.

Veress, et al., *Finite Element Modeling of Atherosclerotic Plaque*, The Cleveland Clinic Foundation, pp. 791-794.

Cheng, et al., *Distribution of Circumferential Stress In Ruptured and Stable Atherosclerotic Lesions A structural Analysis With Histopathological Correlation*, Circulation, vol. 87, pp. 1179-1187 1993.

Lee, et al., *Circumferential Stress and Matrix Metalloproteinase I in Human Coronary Atherosclerosis Implications for Plaque Rupture*, Arteriosclerosis, Thrombosis, and Vascular Biology, vol. 16, pp. 1070-1073 1996.

Vonesh, et al., *Regional Vascular Mechanical Properties by 3-D Intravascular Ultrasound With Finite-Element Analysis*, The American Physiological Society, pp. 425-437 1997.

Beattie, et al., *Mechanical Modeling: Assessing Atherosclerotic Plaque Behavior and Stability in Humans*, International Journal of Cardiovascular Medicine and Science, vol. 2, pp. 68-81 1999.

Freezor, et al., *Integration of Animal And Human Coronary Tissue Testing With Finite Element Techniques For Assessing Differences In Arterial Behavior*, BED, vol. 50 pp. 135-138 2001.

Feezor et al., *Acute Mechanical Response of Human Coronary Fibroatheromas to Stenting*, Summer Bioengineering Conference, 0167-0168, Key Biscayne, FL, (Jun. 25-29, 2003).

\* cited by examiner

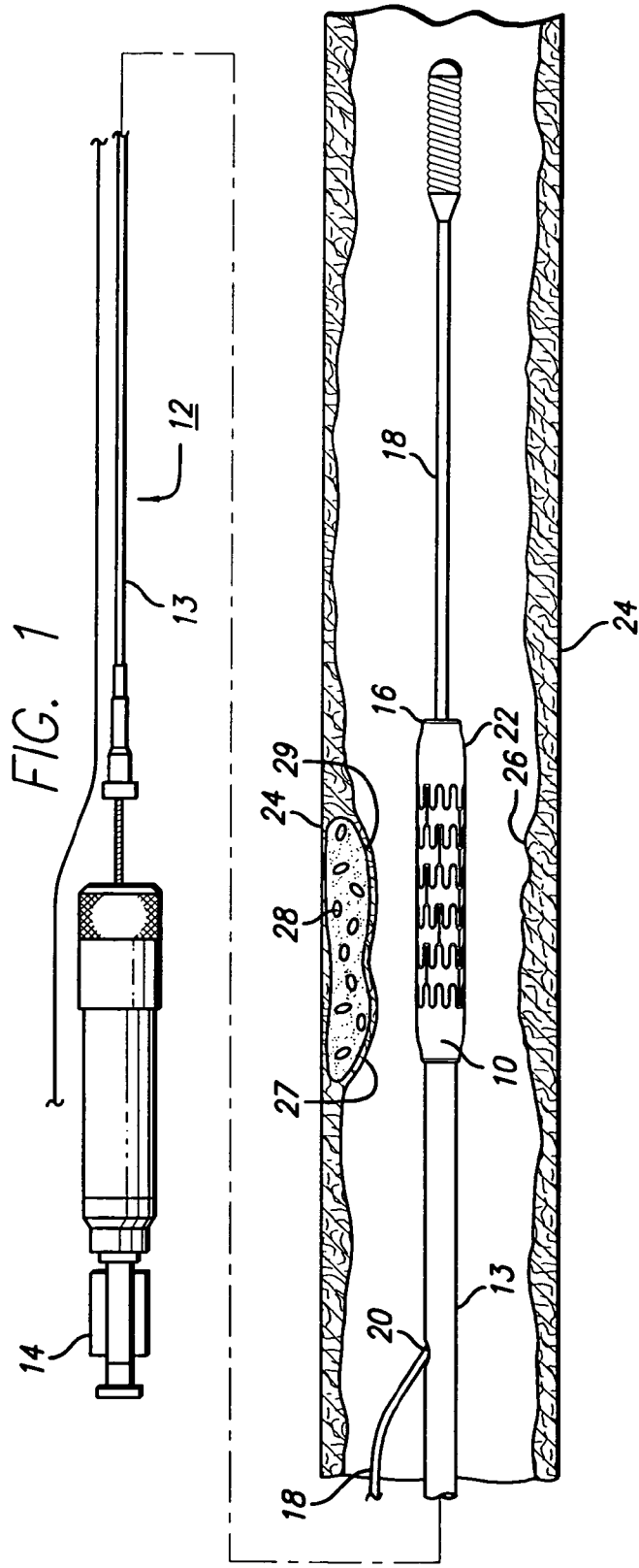
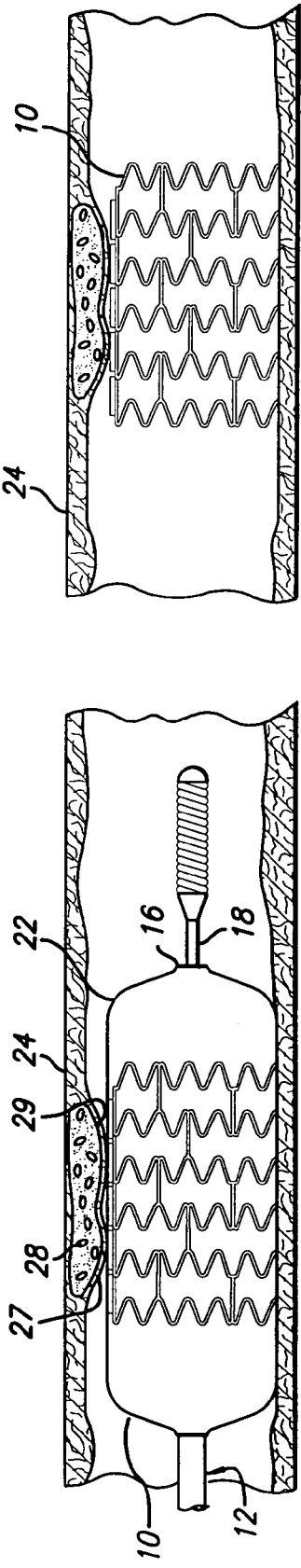
FIG. 1
FIG. 2
FIG. 3

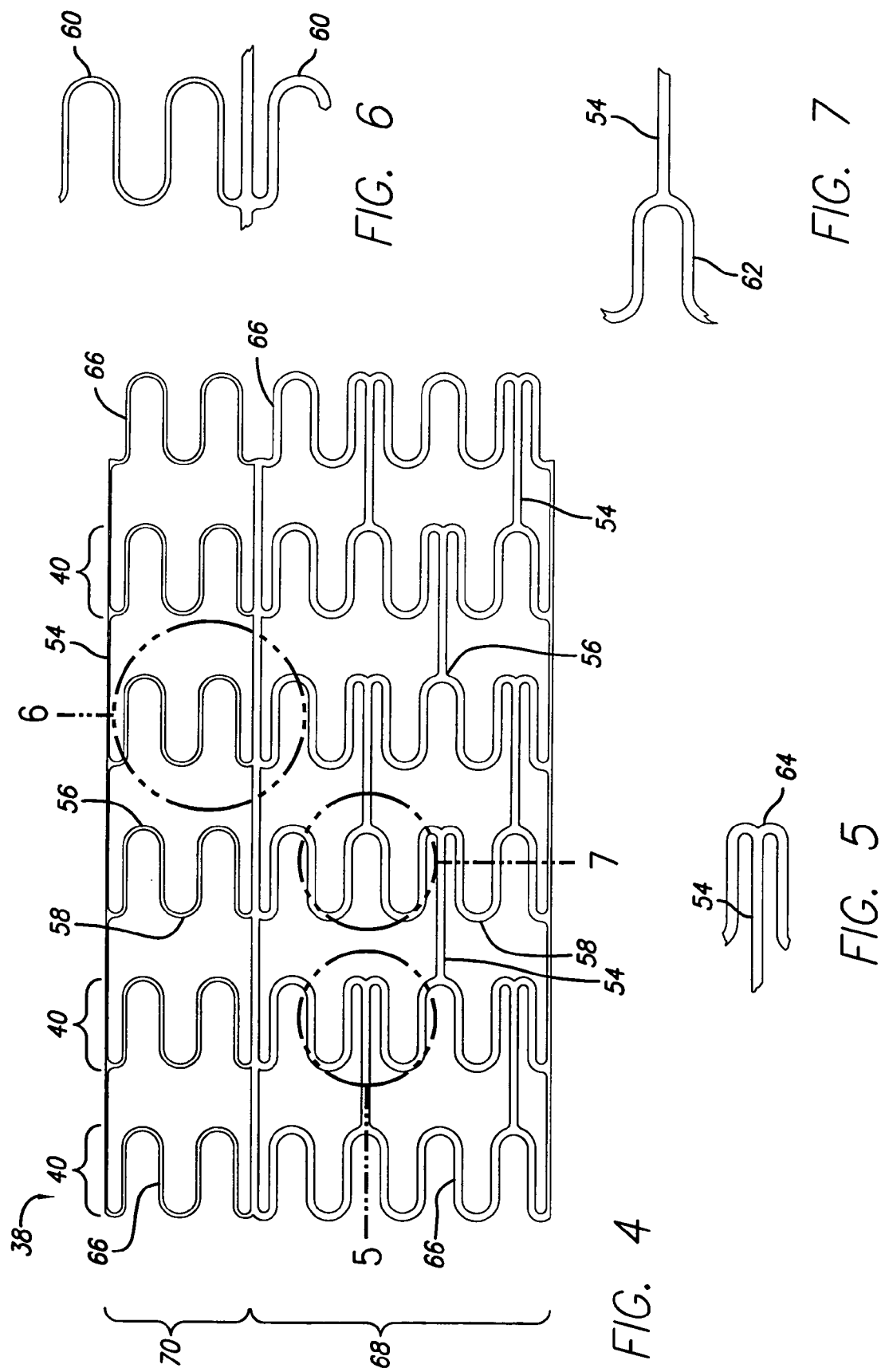

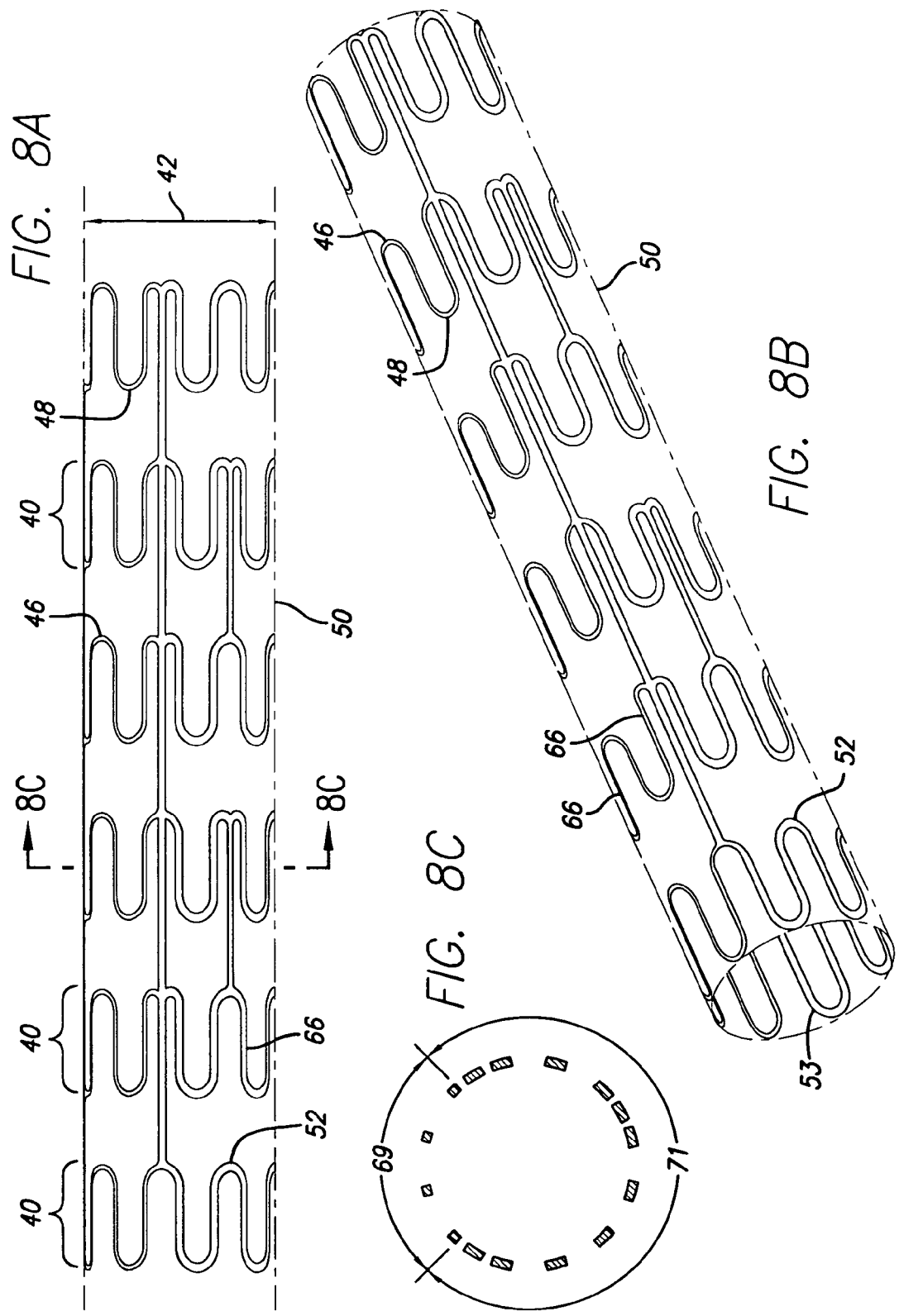

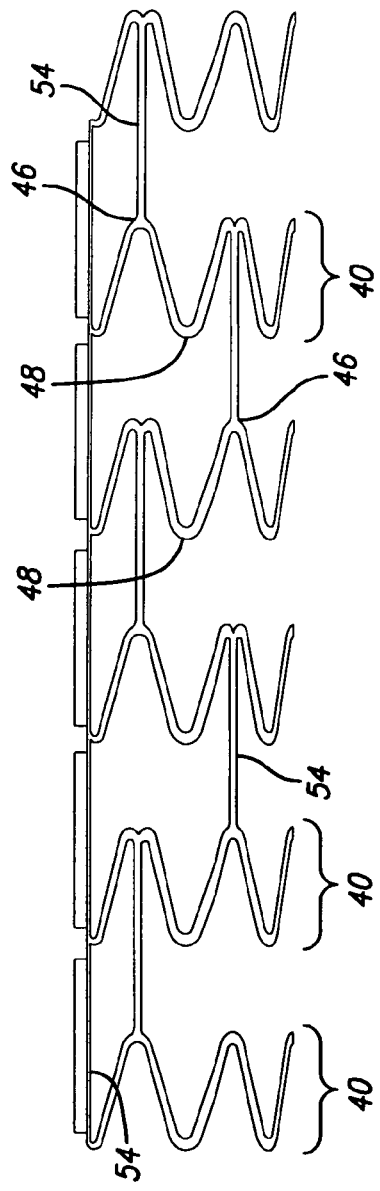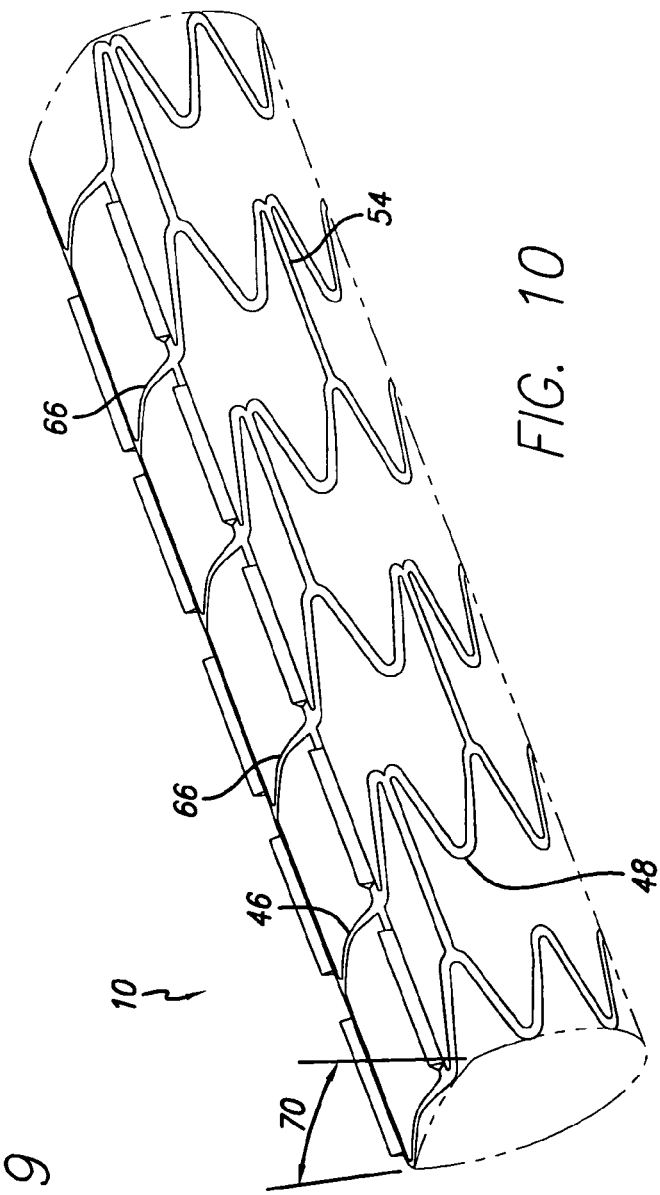

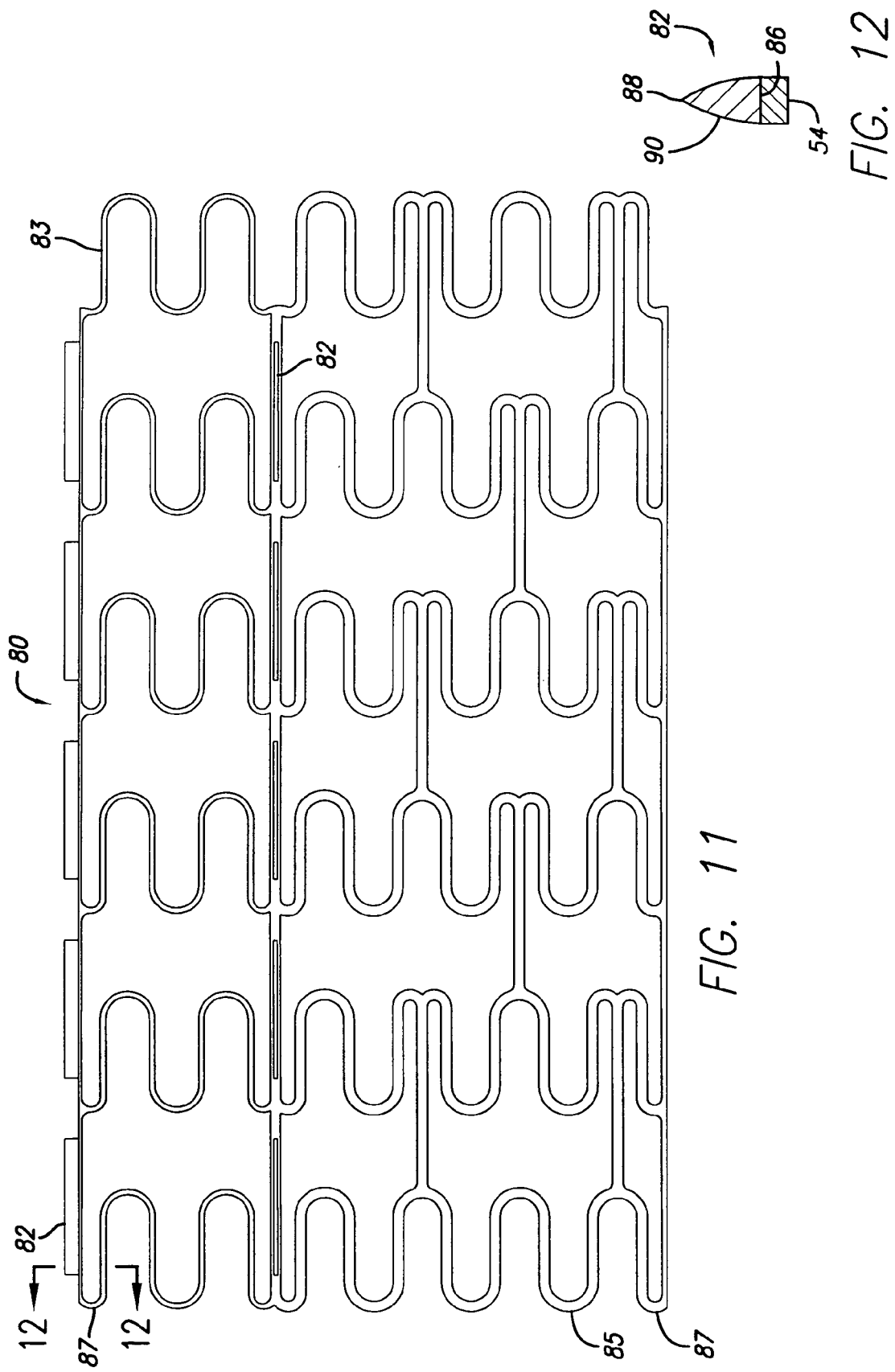

STENT WITH ANCHORS TO PREVENT VULNERABLE PLAQUE RUPTURE DURING DEPLOYMENT

BACKGROUND OF THE INVENTION

The present invention relates to vascular repair devices, and in particular to intravascular stents, which are adapted to be implanted into a patient's body lumen, such as a blood vessel or coronary artery, for the treatment of unstable or vulnerable, human atherosclerotic plaque.

Currently, the treatment of unstable or vulnerable plaque presents a significant therapeutic challenge to medical investigators. Vulnerable plaque is characterized by a basic lesion which is a raised plaque beneath the innermost arterial layer, the intima. Atherosclerotic plaques are primarily composed of varying amounts of long chain extracellular matrix (ECM) proteins that are synthesized by smooth muscle cells. The other primary lesion component of atherosclerotic plaque includes lipoproteins, existing both extracellularly and within foam cells derived primarily from lipid-laden macrophages. In a more advanced lesion, a necrotic core may develop, consisting of lipids, foam cells, cell debris, and cholesterol crystals, and myxomatous configurations with crystalline lipid forms. The necrotic core is rich in tissue factor and quite thrombogenic, but in the stable plaque it is protected from the luminal blood flow by a robust fibrous cap composed primarily of long chain ECM proteins, such as elastin and collagen, which maintain the strength of the fibrous cap. The aforementioned plaque represents the most common form of vulnerable plaque, known as a fibroatheroma. Histology studies from autopsy suggest this form constitutes the majority of vulnerable plaques in humans. A second form of vulnerable plaque represents a smaller fraction of the total, and these are known as erosive plaques. Erosive plaques generally have a smaller content of lipid, a larger fibrous tissue content, and varying concentrations of proteoglycans. Various morphologic features that have been associated with vulnerable plaque, include thinned or eroded fibrous caps or luminal surfaces, lesion eccentricity, proximity of constituents having very different structural moduli, and the consistency and distribution of lipid accumulations. With the rupture of fibroatheroma forms of vulnerable plaque, the luminal blood becomes exposed to tissue factor, a highly thrombogenic core material, which can result in total thrombotic occlusion of the artery. In the erosive form of vulnerable plaque, mechanisms of thrombosis are less understood but may still yield total thrombotic occlusion.

Although rupture of the fibrous cap in a fibroatheroma is a major cause of myocardial infarction (MI) related deaths, there are currently no therapeutic strategies in place to treat these lesions that could lead to acute MI. The ability to detect vulnerable plaques and to treat them successfully with interventional techniques before acute MI occurs has long been an elusive goal. Numerous finite element analysis (FEA) studies have proved that, in the presence of a soft lipid core, the fibrous cap shows regions of high stresses. Representative of these studies include the following research articles, each of which are incorporated in their entirety by reference herein: Richardson et al. (1989), Influence of Plaque Configuration and Stress Distribution on Fissuring of Coronary Atherosclerotic Plaques, Lancet, 2(8669), 941-944; Loree et al. (1992), Effects of Fibrous Cap Thickness on Circumferential Stress in Model Atherosclerotic Vessels, Circulation Research, 71, 850-858; Cheng et al. (1992), Distribution of Circumferential Stress in Ruptured and Stable Atherosclerotic Lesions: A Structural Analysis With Histopathological Correlation, Circulation, 87, 1179-1187; Veress et al. (1993), Finite Element Modeling of Atherosclerotic Plaque, Proceedings of IEEE Computers in Cardiology, 791-794; Lee et al. (1996), Circumferential Stress and Matrix Metalloproteinase 1 in Human Coronary Atherosclerosis: Implications for Plaque Rupture, Atherosclerosis Thrombosis Vascular Biology, 16, 1070-1073; Vonesh et al. (1997), Regional Vascular Mechanical Properties by 3-D Intravascular Ultrasound Finite-Element Analysis, American Journal of Physiology, 272, 425-437; Beattie et al. (1999), Mechanical Modeling: Assessing Atherosclerotic Plaque Behavior and Stability in Humans, International Journal of Cardiovascular Medical Science, 2(2), 69-81; C. Feezor et al. (2001), Integration of Animal and Human Coronary Tissue Testing with Finite Element Techniques for Assessing Differences in Arterial Behavior, BED-Vol. 50, 2001 Bioengineering Conference, ASME 2001; and C. Feezor et al: (2003), Acute Mechanical Response Of Human Coronary Fibroatheromas To Stenting, 2003 Summer Bioengineering Conference, Key Biscayne, Fla., 167-168. Further, these studies have indicated that such high stress regions correlate with the observed prevalence of locations of cap fracture. Moreover, it has been shown that subintimal structural features such as the thickness of the fibrous cap and the extent of the lipid core, rather than stenosis severity are critical in determining the vulnerability of the plaque. The rupture of a highly stressed fibrous cap can be prevented by using novel, interventional, therapeutic techniques such as specially designed stents that redistribute and lower the stresses in the fibrous cap.

Stents are generally tubular-shaped devices which function to hold open a segment of a blood vessel, coronary artery, or other body lumen. They are also suitable for use to support and hold back a dissected arterial lining which can occlude the fluid passageway therethrough.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

Generally speaking, most prior art intravascular stents are formed from a metal such as stainless steel, which is balloon expandable and plastically deforms upon expansion to hold open a vessel. The component parts of these types of stents typically are all formed of the same type of metal, i.e., stainless steel. One of the advantages of the metallic stents is their high radial strength once expanded and implanted in the vessel. When a metallic stent is expanded and implanted in a coronary artery, for example, the stent typically uniformly expands forming a near perfect cylindrical shape which provides a cylindrical lumen for blood flow. The amount of strain imparted to the vessel wall from the prior art metallic stents typically is uniform at all points along the vessel wall, and in particular along the fibrous cap which retains the vulnerable plaque. Since the strains are uniform, the fibrous cap may have a tendency to rupture because it is typically quite thin and is susceptible to the expansion forces of the stent. Thus, one disadvantage of presently designed intravascular stents is the possibility of the stent, which expands uniformly, imparting expansion forces on the fibrous cap to the degree of rupturing the cap, and inadvertently releasing the lipid pool comprising vulnerable plaque.

What has been needed and heretofore unavailable is a stent that can be used to treat a vulnerable plaque by reducing the cap stresses. The present invention satisfies this need and others.

INVENTION SUMMARY

The present invention is directed to an intravascular stent that can be used to treat a lesion with vulnerable plaque by reducing the fibrous cap stresses. The present invention stent in one embodiment provides staged balloon expansion through stronger and weaker regions in the circumference of the stent, and includes anchors positioned at the circumferential transition between the stronger and weaker regions. During implantation, the anchors radially orient and span the weaker region that overlies the fibrous cap of the vulnerable plaque. When embedded in the shoulder area of the fibrous cap, the anchors decouple luminal expansion from stent expansion within defined regions of the fibroatheroma. As a result, the embedded anchors prevent high expansion forces in the weak region from reaching the fibrous cap thus reducing the chance of cap rupture.

In one embodiment, the stent of the present invention includes a plurality of rings that are interconnected with links. The rings are generally aligned along a common longitudinal axis and assume a tubular form. Along the circumference and extending the length of the tube are a first region and a contiguous, non-overlapping second region. Relatively speaking, the first region is weaker with, for example, lesser hoop strength than the second, stronger region with greater hoop strength.

The links are preferably aligned longitudinally (i.e., parallel to the longitudinal axis of the stent) between adjacent rings. The links are further preferably positioned to lie generally coplanar with the outer wall surface of the rings. Anchors are optionally positioned on an outer surface of the links.

The anchors are radially positioned toward the outer periphery of the vessel lesion, such as a shoulder region of the fibrous cap and slightly away from the lipid pool. So oriented, the anchors straddle the fibrous cap while the weaker first region is apposed to the fibrous cap. Initial expansion of the stent causes the weaker first region to circumferentially and radially expand, moving the anchors farther apart. Further stent expansion causes the anchors to embed into the intima adjacent to the fibrous cap, and accordingly, only gentle radial forces are exerted by the weaker first region on the fibrous cap. With the anchors in place, expansion stresses are redistributed to the vessel opposite to the plaque.

Still further expansion causes the stronger second region to engage the remaining vessel wall. Additional anchors, or incisors, may be aligned with the remaining portions of the vessel outside of the vulnerable plaque to induce incisions therein to facilitate greater dilatation of the vessel.

The rings and links can have various configurations. In one embodiment, each of the rings making up the stent has a proximal end, a distal end, and a cylindrical outer wall surface that extends longitudinally between the proximal end and the distal end of the ring. The rings typically are formed from a plurality of peaks and valleys, where the valleys of one ring are circumferentially in phase with the valleys of an adjacent ring. In this embodiment, at least one link attaches each ring to an adjacent ring so that the links are positioned substantially within one of the valleys and attaches the valley to an adjacent valley. While the rings and links generally may or may not have started out as discrete parts, they have been referred to here as rings and links for convenience. The rings can be thought of as comprising a series of U-, W- and Y-shaped structures in a repeating pattern. While the rings are not necessarily divided or segmented into U's, W's and Y's, the wavy patterns of the rings do resemble such forms. The U's, W's and Y's promote flexibility in the stent primarily by flexing and by tipping radially outwardly as the stent is delivered through a patient's often tortuous anatomy.

Preferably, the links are positioned to be within the curved part of the W-shaped portion to generally increase the amount of vessel wall coverage. Since the link does not expand appreciably when the stent is expanded, it provides good vessel wall coverage even as the curved part of the W-shaped portion spreads apart as the stent is expanded.

The rings of the stent in one embodiment are plastically deformed when balloon expanded if the stent is made from a rather inelastic metal. Typically, the balloon expandable stent is made from a stainless steel alloy or similar material.

The stents of the embodiments described above may also be made from a superelastic alloy with the shape memory set in a crimped configuration thereby making the stent self-contracting at body temperature of the patient. Accordingly, the contraction forces of the stent cause the stent to grip onto the balloon.

At the deployment site, the balloon is inflated and the stent expanded in an initial stage which opens the weaker first region of the stent proximate to the fibrous cap of the vulnerable plaque, and a subsequent stage which opens the second region of the stent to expand the remaining portion of the vessel.

The stent may be formed by laser cutting the pattern of rings and links from a tube. The stent also may be formed by laser cutting a flat metal sheet into a pattern of the rings and links, and then rolling the pattern into the shape of the tubular stent. The longitudinal seam where the edges of the sheet meet is then welded or otherwise joined.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a side elevational view, partially in section, of a stent embodying features of the invention and which is mounted on a rapid-exchange delivery catheter and positioned within an artery.

FIG. 2 is a side elevational view, partially in section, similar to that shown in FIG. 1 wherein the stent is balloon expanded within the artery so that the stent embeds within the arterial wall.

FIG. 3 is a side elevational view, partially in section, showing the expanded stent implanted within the artery after withdrawal of the rapid-exchange delivery catheter.

FIG. 4 is a plan view of one embodiment of the present invention stent shown in FIGS. 1-3, flattened into two dimensions to illustrate the strut pattern.

FIG. 5 is an enlarged sectional view of FIG. 4 depicting a W-shaped portion of the ring.

FIG. 6 is an enlarged sectional view of FIG. 4 depicting a U-shaped portion of the ring.

FIG. 7 is an enlarged sectional view of FIG. 4 depicting a Y-shaped portion of the ring.

FIG. 8A is a side elevational view of a stent embodying features of the invention in an unexpanded state.

FIG. 8B is a perspective view of the stent of FIG. 8A depicting a cylindrical wall defined by the rings.

FIG. 8C is cross-sectional view taken along line 8C-8C in FIG. 8A depicting the radial arrangement of the struts.

FIG. 9 is a side elevational view of the stent of FIG. 8A in an expanded condition.

FIG. 10 is a perspective view of the stent of FIG. 8A in an unexpanded condition.

FIG. 11 is a plan view of a stent flattened into a sheet to illustrate anchors positioned on links.

FIG. 12 is an enlarged cross-sectional view taken along line 12-12 of FIG. 11 of one embodiment of an anchor.

DETAILED DESCRIPTION OF THE PREFERRED EMBODIMENTS

Figure 14C:
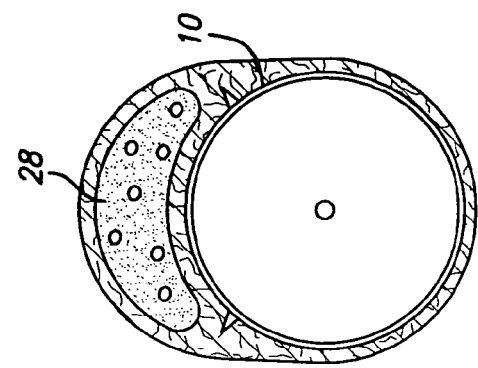
FIG. 14C is an end view, partially in section, showing the stent of FIG. 14B after subsequent expansion of the stronger second region of the stent to engage the remaining vessel wall around the fibrous cap.

The present invention is directed to an intravascular stent that can be used to treat a lesion with vulnerable plaque by minimizing the cap stresses during stent expansion. The present invention stent in one embodiment provides staged balloon expansion through stronger and weaker regions in the cylindrical wall of the stent, and includes anchors positioned at the circumferential transition between the stronger and weaker regions. During implantation, the anchors radially orient and span the weaker region over the vulnerable plaque during the staged expansion. This minimizes cap stresses and reduces the chance of cap rupture.

Turning to the drawings, FIG. 1 depicts one embodiment of the present invention stent 10 mounted on a catheter assembly 12 which is used to deliver the stent and implant it in a body lumen, such as a coronary artery, peripheral artery, or other vessel or lumen within a patient's body. The catheter assembly 12 includes a catheter shaft 13 which has a proximal end 14 and a distal end 16. The catheter assembly 12 is designed to advance through a patient's vascular system by tracking over a guide wire by any of the well-known methods for an over the wire system (not shown) or a well-known rapid exchange catheter system, such as the one shown in FIG. 1.

The catheter assembly 12, as depicted in FIG. 1, is of the rapid exchange (RX) type, which includes an RX port 20 where the guide wire 18 exits the catheter at the distal end 16. This way, the catheter 12 advances along the guide wire 18 on a section of the catheter between the RX port 20 and the catheter distal end 16. As is known in the art, the guide wire lumen which receives the guide wire 18 is sized for receiving various diameter guide wires to suit a particular application. The stent 10 is mounted on the balloon or expandable member 22 and is crimped tightly thereon so that the stent 10 and expandable member 22 present a low profile diameter for delivery through narrow or tortuous arteries.

FIG. 1 illustrates a partial cross-section of an artery 24, which is shown with a small amount of plaque, a lesion, or a diseased area 26 that has been previously treated by an angioplasty or other repair procedure. The stent 10 is used to repair this diseased or damaged area 26.

The stent 10 may also be used to treat an area with vulnerable plaque 27 which is commonly found in the coronary arteries, peripheral arteries, and other vessels. Vulnerable plaque 27 consists of a thrombogenic lipid 28 that is covered by a thin fibrous cap 29. The stent 10 is configured to deploy in stages so as to protect the vulnerable plaque 27 from the expansion forces of the stent 10, thereby reducing the likelihood of inadvertently rupturing the fibrous cap 29 and causing the lipid pool 28 to drain. The stent 10 also allows the fibrous cap 29 to thicken after stent deployment, further reducing the likelihood of a rupture.

In a typical procedure to implant the stent 10, the guide wire 18 is advanced through the patient's vascular system so that the distal end of the guide wire 18 is advanced past the vulnerable plaque 27 or diseased area 26. Prior to implanting the stent 10, a cardiologist may wish to perform an angioplasty procedure or other procedure (i.e., atherectomy) in order to open the vessel and reshape the diseased area 26. Thereafter, the stent delivery catheter assembly 12 is advanced over the guide wire 18 so that the stent 10 is positioned in the target area. Generally, the expandable member or balloon 22 is inflated so that it expands radially thereby expanding the stent 10 radially until the stent is apposed to the vessel wall. The expandable member 22 is then deflated and the catheter 12 withdrawn from the patient's vascular system. The guide wire 18 is typically left in the lumen for post-dilatation procedures, if any, and is subsequently withdrawn from the patient's vascular system.

As depicted in FIG. 2, the balloon 22 is fully inflated with the stent 10 expanded and engaging the vessel wall. In FIG. 3, the implanted stent 10 remains in the vessel after the balloon 22 has been deflated and the catheter assembly 12 and guide wire 18 have been withdrawn from the patient. As further illustrated in FIGS. 2 and 3, the vulnerable plaque 27 is left intact without rupture of the lipid pool 28.

The stent 10 serves to hold open the artery after the catheter 12 is withdrawn, as illustrated by FIG. 3. Due to the construction of the stent 10 from a generally elongated tube, the undulating struts of the stent 10 are relatively flat in a transverse cross-section, so that when the stent 10 is expanded, it is pressed into the wall of the artery and as a result does not interfere with the blood flow through the artery. The stent 10 is pressed into the wall of the artery and will eventually be covered with smooth muscle cell growth which further minimizes blood flow interference. The undulating struts of the stent also provide good tacking characteristics to prevent stent movement within the artery.

FIGS. 4-10 depict various embodiments of the present invention stent. Turning specifically to FIG. 4, the stent is shown as a flattened sheet so that the strut pattern can be clearly seen, even though the stent is usually not in this form unless it is created from a flat sheet. If formed from a flat sheet, the sheet is rolled into a cylindrical configuration and welded or joined at the longitudinal seam.

On the other hand, the present invention stent is preferably fashioned from a tube. Conceptually, the tubular form is made from a plurality of rings aligned coaxially along a common longitudinal axis. The rings are joined by interconnecting links.

With respect to the structure of the rings and links, virtually any pattern is acceptable. Typically, the rings are in the form generally of an undulating or serpentine strut pattern 38 that can easily expand radially outward or compress radially inward. Thus, as described immediately below, an example of rings 40 and links 54 are described. Of course, other patterns are envisioned that would perform equally as well in protecting the vulnerable plaque 27 and supporting the vessel 24.

As shown in FIGS. 4-10, the stent 10 is made up of a plurality of rings 40 aligned coaxially when it is in a tubular form (see FIGS. 8A and 8B). The stent has a delivery diameter 42 as shown in FIG. 8A, and an implanted configuration as shown in FIG. 9. Each ring 40 has a ring proximal end 46 and a ring distal end 48. In a preferred embodiment, the stent is laser cut from a single tube so there are no discrete parts such as the described rings.

Each ring 40 defines a portion of a cylindrical surface 50, which collective is a hypothetical surface (dashed lines in FIGS. 8A, 8B) terminating at the longitudinal limits by the proximal and distal ends 46, 48, and limited circumferentially by the outside diameters of the rings 40. Each ring 40 includes a cylindrical outer wall surface 52 that defines the outermost surface of the stent, and a cylindrical inner wall surface 53 which defines the innermost surface of the stent. The cylindrical surface 50 preferably coincides with the cylindrical outer wall surface 52. In this embodiment, the links 54 generally lie within the cylindrical surface 50. Further, the links 54 interconnect, join, or bridge one ring 40 to an adjacent ring 40.

Rings 40 with their strut patterns can be nested such that adjacent rings slightly overlap in the longitudinal direction. The degree of nesting is dictated primarily by the length of each ring, the number of strut undulations in the rings, the thickness of the struts that make up the rings, and the radius of curvature, all in conjunction with the crimped or delivery diameter of the stent. If the rings are substantially nested one within the other, it may be difficult to crimp the stent to an appropriate low profile delivery diameter without the various struts overlapping. It is also contemplated that the rings are slightly nested even after the stent is expanded, which enhances vessel wall coverage. In some circumstances, it may not be desirable to nest one ring within the other, which is also contemplated by the invention.

Referring to FIGS. 4-10, the stent 10 can be described more particularly as having a plurality of peaks 56 and valleys 58. Although the stent 10 is preferably not divided into separate and discrete components, for ease of discussion, references to peaks 56 and valleys 58 are appropriate.

The number of peaks and valleys can vary in number for each ring depending upon the application. For example, if the stent is to be implanted in a coronary artery, a lesser number of peaks and valleys are required than if the stent were implanted in a peripheral artery, which generally has a larger diameter than a coronary artery. As can be seen in FIG. 4, the peaks 56 from ring to ring are in phase, meaning that the peaks 56 from ring to ring all point in the same direction, and are substantially aligned along a line which is parallel to the longitudinal axis of the stent. It may be desirable under certain circumstances to position peaks 56 so that they are out of phase (not shown); that is, the peaks of adjacent rings are circumferentially offset such that the peaks of one ring are not aligned with the rings of an adjacent ring. As shown in FIG. 4, the peaks are substantially circumferentially aligned and in phase. Positioning the peaks, valleys, and links in this manner, provides a longitudinally flexible stent having uniform expansion capabilities, high radial strength and sufficient wall coverage to support the vessel. The same in-phase and out-of-phase construct can be used to describe valleys 58 as well.

In one embodiment, links 54 connect adjacent rings 40 between circumferentially aligned valleys 58, or alternatively between circumferentially aligned peaks 56, wherein the links 54 are circumferentially aligned between adjacent rings 40. Alternatively, the links 54 may connect adjacent rings 40 between alternating valleys 58 or peaks 56 with the link pattern being circumferentially offset between adjacent rings (not shown). The links may be substantially straight and extend substantially parallel to the longitudinal axis of the stent. Alternatively, the links may include an undulating section 102 (see FIGS. 17 and 18).

Referring to FIGS. 5-7, each ring 40 can be more precisely described as being formed from a U-shaped portion 60, a Y-shaped portion 62, and a W-shaped portion 64, or any one or combinations thereof. Accordingly, while the stent is preferably laser cut from a tube and typically has no discrete parts, for ease of identification, the exemplary stent can be referred to as having U-, Y-, and W-shaped portions. The U-shaped portion 60 has no supporting structure attached thereto. The Y-shaped portion 62, at its base or apex, has a link 54 extending therefrom. The W-shaped portion 64 has a link 54 attached at its base or curve portion. The length of the link 54 can vary depending upon the desired amount of separation and nesting between adjacent rings. Preferably, the link 54 is contained within the W-shaped portion 64, which should be wide enough to accommodate the link when the stent is crimped so that no portion of the link and the W-portion overlap. Preferably, the link 54 and the W-shaped portion 64 generally lie in the same cylindrical surface 50 as physically embodied by the cylindrical outer wall surface 52.

The stent 10 is formed so that struts 66 have variable thickness, width, or length, or any combination thereof. In order to create relatively weak and strong circumferential regions, it is contemplated that the stent includes a weak first region 70 which spans a first angular distance or arc 69 (FIG. 8C) along the circumference of the stent, and a strong second region 68 which spans a second angular distance or arc 71 (FIG. 8C) along the circumference of the stent.

Typically, the terms weak and strong imply that the struts comprising the ring gives the ring lesser or greater hoop strength, respectively. Another interpretation for the weak and strong labels is that struts that are more flexible are weak and stiffer struts are strong.

As such, the struts 66 in the strong second region 68 may be thicker, wider and/or larger than the struts in the remaining weak first region 70. This difference in strut construction causes the second region 68 to be stronger than the first region 70. Similarly, the links 54 falling in the strong second region 68 may also be larger or wider than the links 54 falling in the weak first region 70 of the stent. Additional control of the strength between the first 70 and second 68 regions of the stent may be attained by varying the radii of the peaks 56 and valleys 58 of the rings 40. Still other ways of strengthening or weakening the struts and rings can be accomplished by techniques known in the art.

With the first 70 and second 68 regions of the stent 10 having different strengths, the stent opens in stages. More particularly, the portion of the balloon 22 apposed to the weak first region 70 of the stent 10 has a tendency to inflate at a faster rate than the portion of the balloon 22 apposed to the strong second region 68 of the stent. Thus, the weak first region 70 expands circumferentially substantially to its fully deployed state before the strong second region 68.

During a dilatation procedure, the weak first region 70 of the stent is substantially aligned with the diseased portion of a vessel, such as the vulnerable plaque 27 in an artery 24, before expansion of the stent is commenced. The first region 70 expands preferentially before the second region 68 so adjustments to the stent alignment can be made during expansion of the first region 70. In one embodiment of the invention, the weak first region 70 expands substantially to its fully deployed state, such as an arcuate but nearly straight condition, prior to the substantial expansion of the strong second region 68. This prevents the first region 70 from expanding further. All of these features protect the fibrous cap 29 of the vulnerable plaque 27 from inadvertent rupture due to expansion stresses exerted by the stent.

Figure 13:
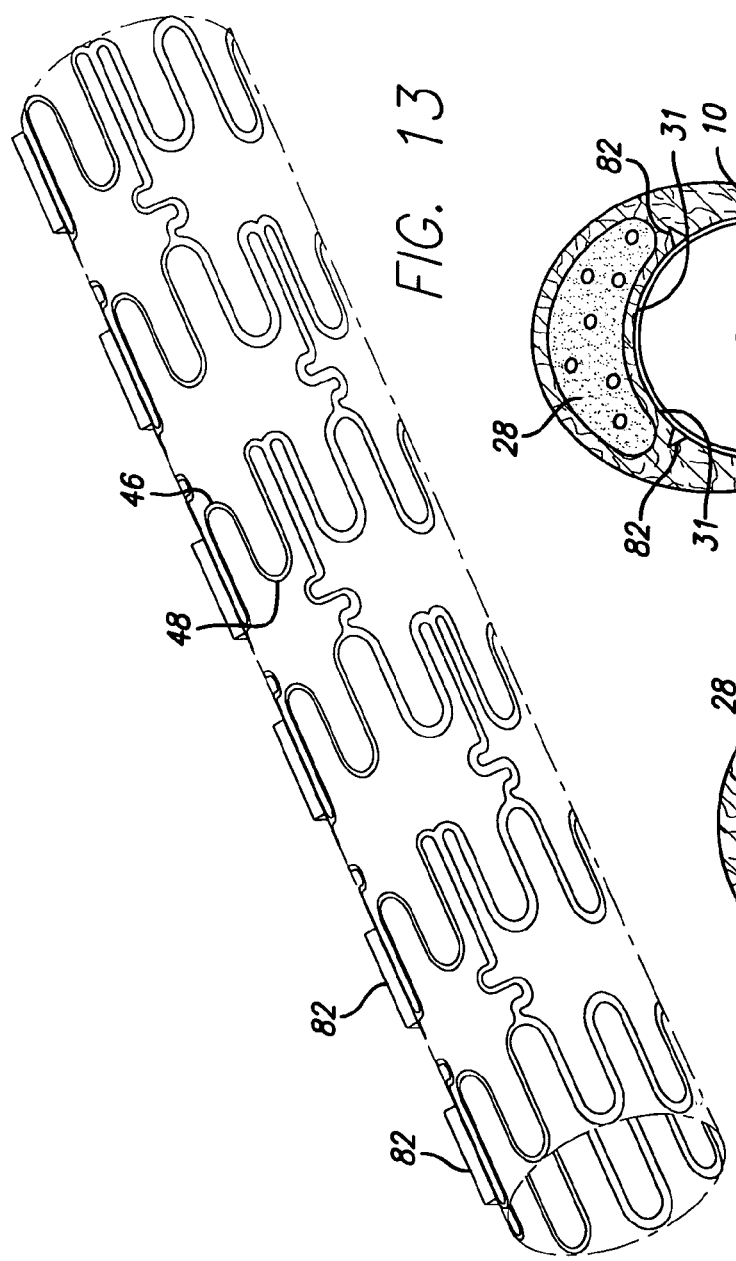
FIG. 13 is a perspective view of the stent of FIG. 11 in an unexpanded state.

Referring to FIGS. 11-13, the stent 10 also includes optional anchors 82. In a preferred embodiment, the anchors 82 take the form of incisors positioned on the outer surfaces of the links 54. The anchors 82 embed into the vessel wall. Ideally, the anchors 82 are intended to embed into the shoulder area or just outside at the periphery of the fibrous cap 29 so that the cap is not injured or ruptured.

During the first stage of deployment (see FIGS. 14A-14C), the stent is rotationally oriented so that the lipid pool 28 of the vulnerable plaque 27 is located between the anchors 82 and with the weak first region 70 positioned overlying the vulnerable plaque 27. As explained above, the milder expansion forces exerted by the weak first region 70 minimizes the stresses conveyed to the fibrous cap 29.

Figure 14B:
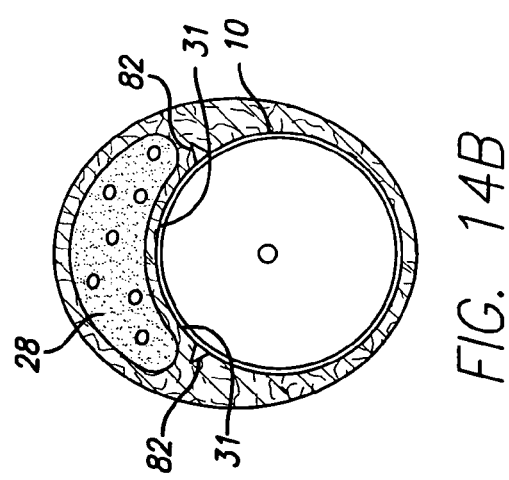
FIG. 14B is an end view, partially in section, showing the stent from FIG. 14A after initial expansion of the weaker first region and implantation of the anchors at the shoulders of the fibrous cap.
Figure 14A:
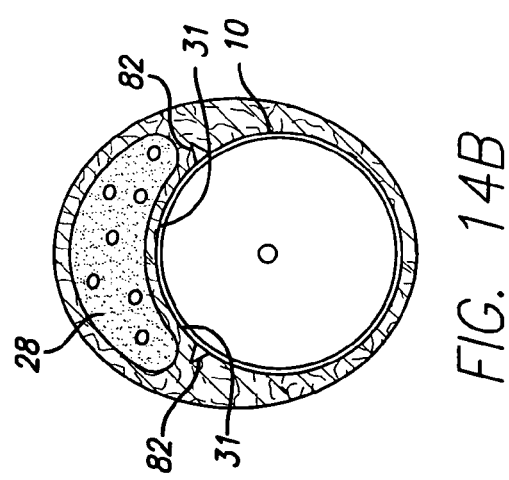
FIG. 14A is an end view, partially in section, showing the stent of FIG. 11 positioned within the artery where the weaker first region faces the vulnerable plaque prior to expansion of the stent.

As the first region 70 approaches its fully deployed state during expansion of the stent, the anchors 82 are spread farther apart and straddle the fibrous cap 29. This is shown in FIGS. 14A and 14B. Ultimately, the anchors 82 penetrate the vessel wall and/or a shoulder region 31 at the periphery of the fibrous cap 29, which region 31 is away from the lipid pool 28. Once anchored, the expanding stent is positively oriented so that the first region 70 overlies the fibrous cap 29 and further expansion of the first region 70 is avoided.

During the second stage of stent deployment, the first region 70 of the stent is substantially fully deployed. The stronger second region 68 is now expanded into the remaining vessel wall away from the fibrous cap 29. Hence, the luminal expansion which is required to restore vessel lumen patency is forced to occur at a desirable distance away from the lipid pool of the vulnerable plaque.

The anchors 82 may also create incisions in the vessel wall which may relieve stress in the vessel wall and enhance dilatation in the regions of the vessel without a vulnerable plaque. These incisions, as seen in the end views of FIGS. 14B, 14C, straddle or are on either side of the fibrous cap 29. The anchors 82 are thus situated at the circumference of the stent in such a manner as to avoid penetrating or injuring the fibrous cap 29.

Referring again to FIGS. 11-13, one exemplary embodiment includes anchors 82 positioned lengthwise on the links 54 that are also aligned lengthwise along the longitudinal length of the stent. In this arrangement, the position of the links 54 and the anchors 82 coincides with the linear transitions 87 between the first region 70 and the second region 68 of the stent 10. Since the stent is substantially cylindrical, there are typically two linear transitions 87 coinciding with the two interfaces between the first and second regions 70, 68 at the circumference of the stent.

With the anchors 82 positioned at the transitions between the first 70 and second 68 regions, the anchors 82 may be set into the vessel wall at the completion of the first expansion stage, thereby substantially preventing further expansion of the first region 70 during the second expansion stage. Additional anchors or incisors may be positioned along the length of the stent on links positioned within the second region 68 of the stent to enhance dilatation of the remaining regions of the vessel.

To reduce the tendency of the anchors 82, or incisors, to scrape the vessel wall during expansion of the stent 10, the links 54 upon which the anchors 82 are coupled are arranged parallel to the longitudinal axis of the stent. This also prevents or minimizes circumferential movement of the links 54 during expansion.

In the embodiment shown in FIG. 11, the link pattern includes at least one series of aligned links 54 forming an uninterrupted bar extending parallel to the longitudinal axis of the stent from a proximal ring 83 of the stent to a distal ring 85 of the stent. The stent preferably includes a plurality of links arranged in this fashion to create multiple bars running along the length of the stent. The anchors 82 are aligned lengthwise with the links 54 to achieve linear, longitudinal incisions in the vessel wall that are aligned with the longitudinal axis of the stent.

Although the number, size, and location of the anchors 82, or incisors, depend on the stent design, a continuous incisor (not shown) along the length of the stent creates a clean incision along which the artery may expand. However, an anchor 82 that extends the length of the stent adds bulk and increases the bending moment, thereby possibly stiffening the stent undesirably. In a preferred embodiment, the height of the anchors 82 is between about 50 to about 100 microns, inclusive, although the height may be greater.

The bending and expansion stiffness of the stent attributable to the anchors may be reduced by separating the incisors into a series of shorter segments such as that shown in FIGS. 11 and 13. Accordingly, there is a small gap between adjacent anchors, yet collectively the anchors can make a single incision in the vessel wall. Alternatively, or in combination, the stiffness may be reduced by making the anchors, or incisors, from a shape memory material, such as a superelastic nickel-titanium alloy.

As shown in the cross-sectional view in FIG. 12, the anchor 82 includes a spine 86 which is coupled to the outer surface of a link 54 and a cutting edge 88 that projects radially outward from the longitudinal axis of the stent. To form a somewhat wedge-like profile, the sides 90 of the anchor 82 are convex, but may alternatively be concave or flat. As seen in the plan view of FIG. 11, the anchors 82 have a generally long and skinny base; the length is substantially greater than the width. In the preferred embodiment, the base of the anchor 82 sits flush with the sides of the link 54 beneath.

Naturally, in various alternative embodiments, the base of the anchor may be larger or smaller than the area offered by the link. Anchors can also be placed at other locations on the stent such as at a strut, a peak, a valley, etc. One rationale for placing the anchors along the links that are aligned with the longitudinal axis of the stent is that throughout expansion, the links remain substantially aligned with the longitudinal axis. This longitudinal alignment is well suited for limiting lateral expansion of the first region, for example. If the anchors are placed on a strut, outward expansion of the stent causes the struts that may have been initially aligned with the longitudinal stent axis to now become skewed relative to that axis as the undulating pattern unfolds and straightens. This effect can be observed by looking at the unexpanded struts 66 in FIG. 8 versus the expanded struts 66 in FIG. 10. Indeed, the struts 66 in the first region 70 have expanded to a point that they almost appear straight after rotating nearly 90 degrees.

Back in FIG. 12, the height and relatively pointed cutting edge 88 of the anchor 82 are sufficient to make an incision in the vessel wall to facilitate dilatation of the vessel. The height of the anchor 82 should also be sufficient for relatively deep penetration into the vessel wall. This prevents unintended lateral movement of the stent and limits further expansion of the first region of the stent after the anchors are imbedded into the vessel wall. To protect the vessel walls until the stent is positioned for deployment, a sheath or other protective covering may optionally be used to cover the stent during delivery to the lesion.

Referring again to FIGS. 14A-14B, the stent 10 is deployed by positioning the stent in the vessel 24 proximate the vulnerable plaque 27 and aligning the weak first region 70 of the stent with the vulnerable plaque. Aligning the first region 70 of the stent 10 with the vulnerable plaque 27 may be facilitated through the use of guidance equipment, such as optical coherence tomography or other equipment well known in the art. With the stent 10 oriented as desired, the balloon 22 may begin to be inflated, thereby expanding the first region 70. The first region 70 is expanded until it is substantially fully deployed and the anchors 82 are embedded into the vessel wall. Continued inflation of the balloon 22 expands the second region 68 of the stent and may further embed the anchors 82 into the vessel wall. The healing process which follows deployment of the stent may reinforce the fibrous cap 29 of the vulnerable plaque 27 by allowing neointima growth over the first region of the stent, thereby also allowing neointima growth over the fibrous cap 29.

In other embodiments of the invention, the stent 10 may include links which provide greater flexibility to the stent than the substantially straight links 54 depicted in FIG. 4 which form a substantially straight bar along the length of the stent. In one embodiment illustrated in FIG. 17, the links 100 include an undulating portion 102 positioned between adjacent rings 40 with the links 100 positioned at the transitions between the first 70 and second 68 regions of the stent 10 being longitudinally aligned along the length of the stent. The undulating portions 102 of the links 100 provide greater flexibility along the length of the stent. This greater flexibility helps compensate for the possible increased stiffness as a result of adding anchors to the links.

Figure 17:
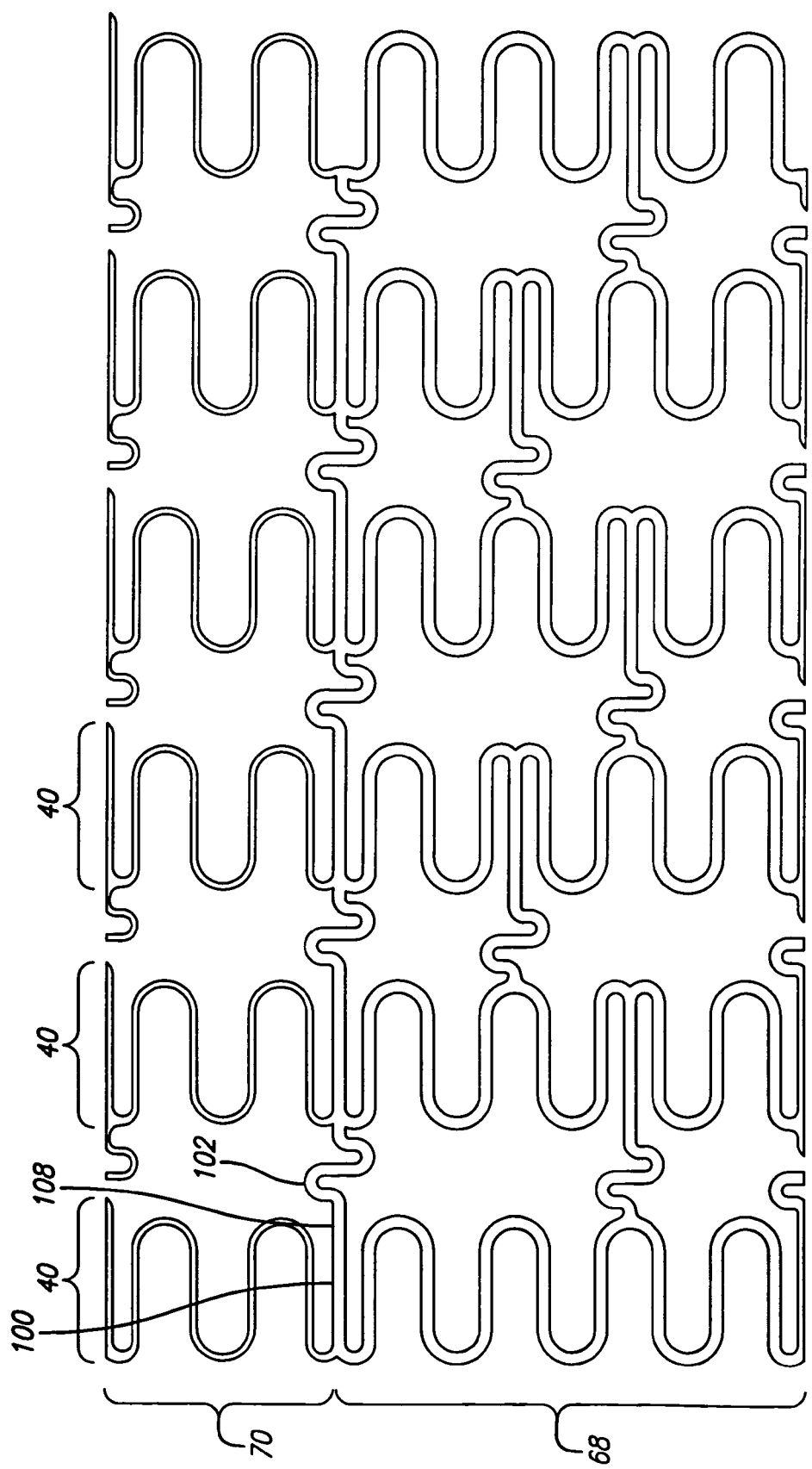
FIG. 17 is a plan view of a flattened stent of another embodiment of the invention which depicts links having an undulating portion positioned between rings.
Figure 18:
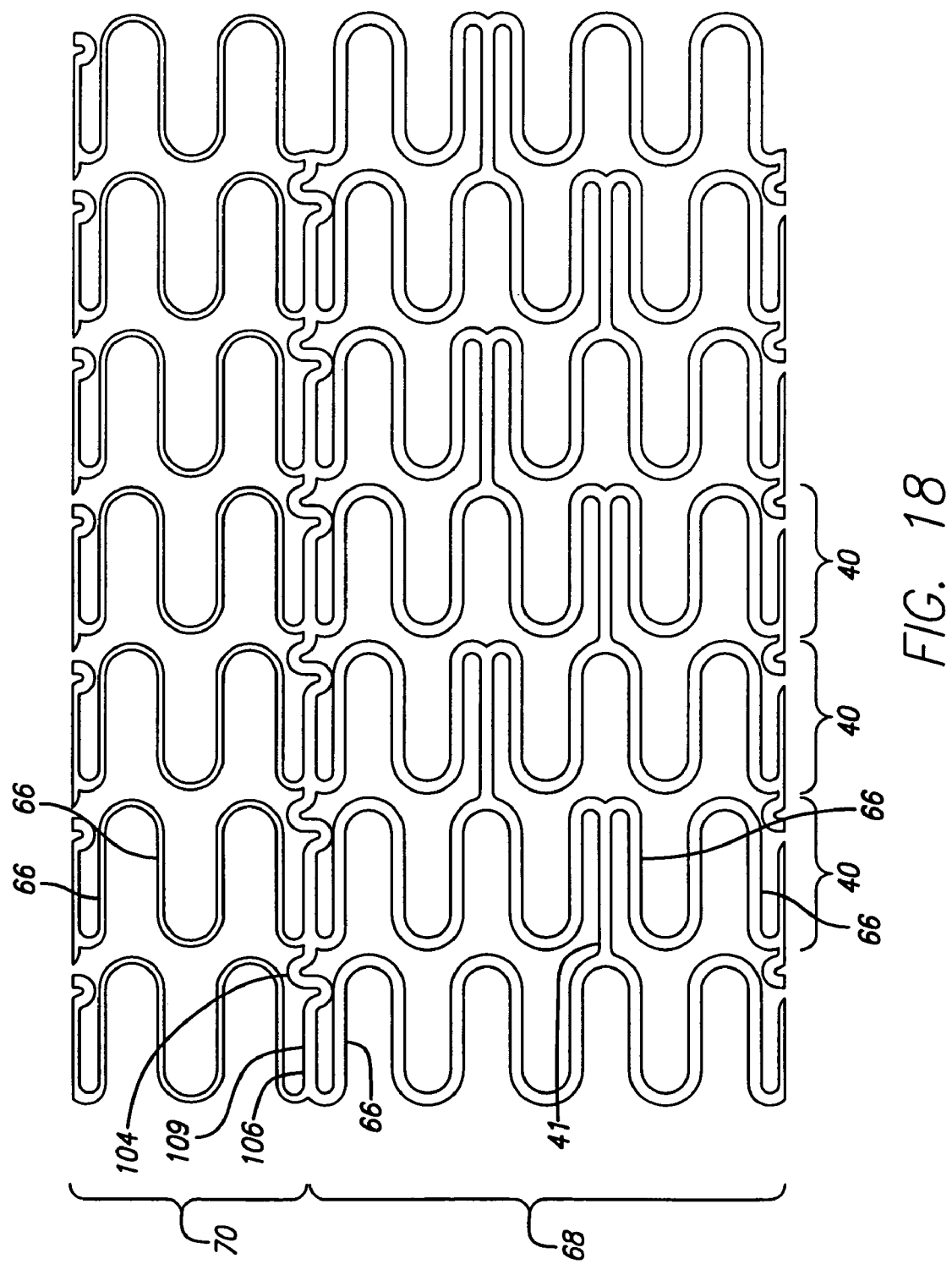
FIG. 18 is a plan view of a flattened stent of another embodiment of the invention which depicts links having undulating portion positioned between the struts of a ring.

In an alternative embodiment, an undulating portion 104 of a link 106 is positioned between the struts 66 of one of the rings 40 (FIG. 18). Further, the links 106 positioned within the first region 70 of the stent may be arranged in an alternating pattern along the length of the stent (FIGS. 17 and 18). The anchors (not shown) are positioned on the straight portions 108, 109 of the links 100, 106 in the embodiments of FIGS. 18, 19. The invention also contemplates the use of various link configurations within the stent to meet varying needs, such as for flexibility or vessel coverage.

Other ring configurations having varying strengths about the circumference of the stent are also contemplated by the invention. In one embodiment of the invention seen in FIG. 19, the rings 110 of the stent 112 include reinforcing members 114 located in the weak first region 70. The circumferential sections of the rings 110 in the weak first region 70 preferably have an undulating strut pattern with peaks 56 and valleys 58. The reinforcing member 114 also preferably includes an undulating pattern including a valley 116 with legs that subtend the struts and peak 56 in the ring 110. Although the struts in the first region 70 are thinner and weaker than the wider, stronger struts in the second region 68, the reinforcing members 114 more precisely control the strength of the stent in the first region 70, and improve vessel coverage in the section apposed to the fibrous cap 29.

The geometry of the reinforcing members 114 can assume many configurations. For example, a reinforcing member could include a loop that curves toward or away from the peaks 56 or valleys 58 of the second region of the rings. In another embodiment, the ends of each reinforcing member of a ring are aligned along a plane which is perpendicular to the longitudinal axis of the stent.

Figure 19:
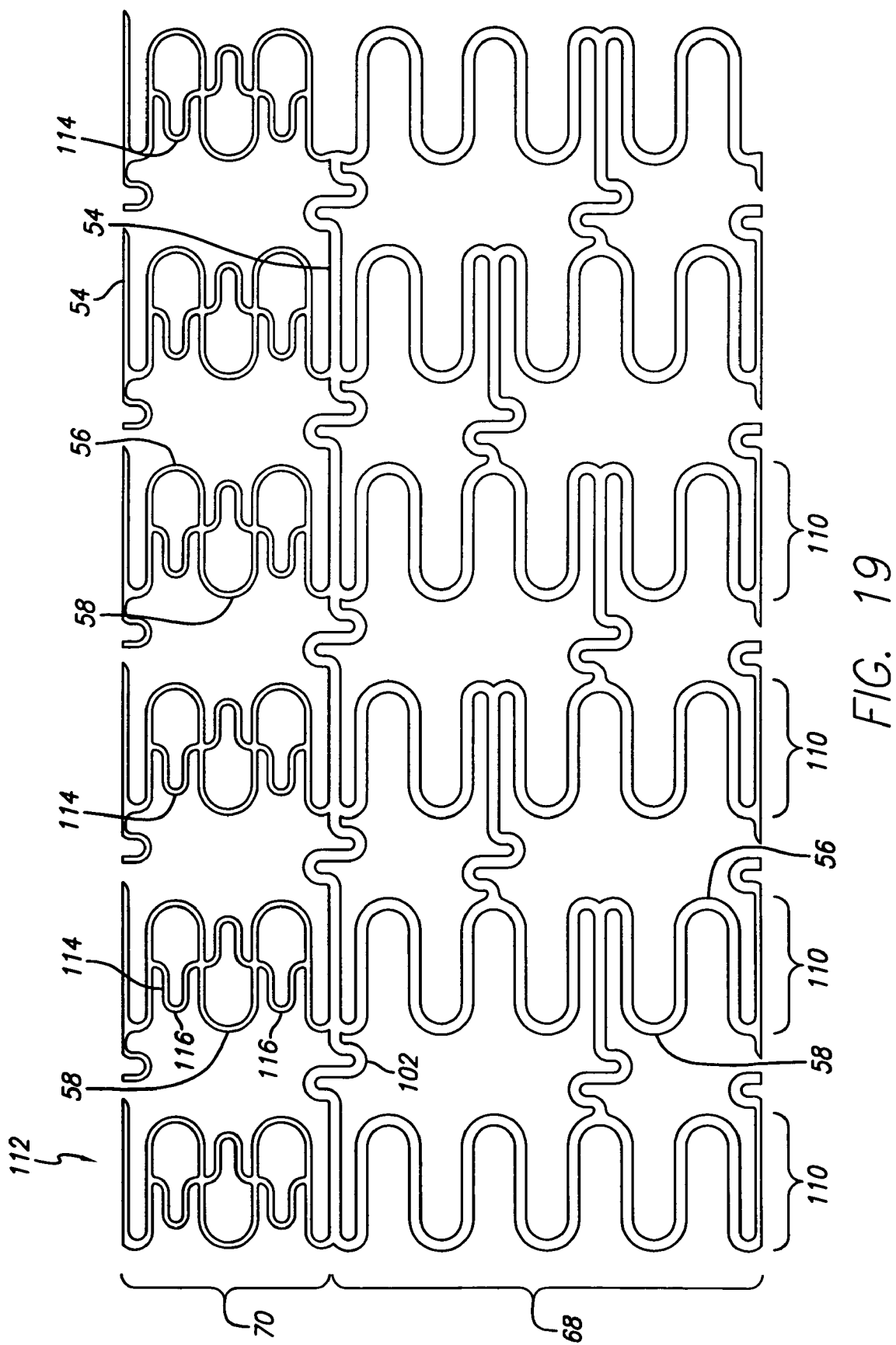
FIG. 19 is a plan view of a flattened stent of another embodiment of the invention having reinforcing members positioned between the struts of the rings.
Figure 20:
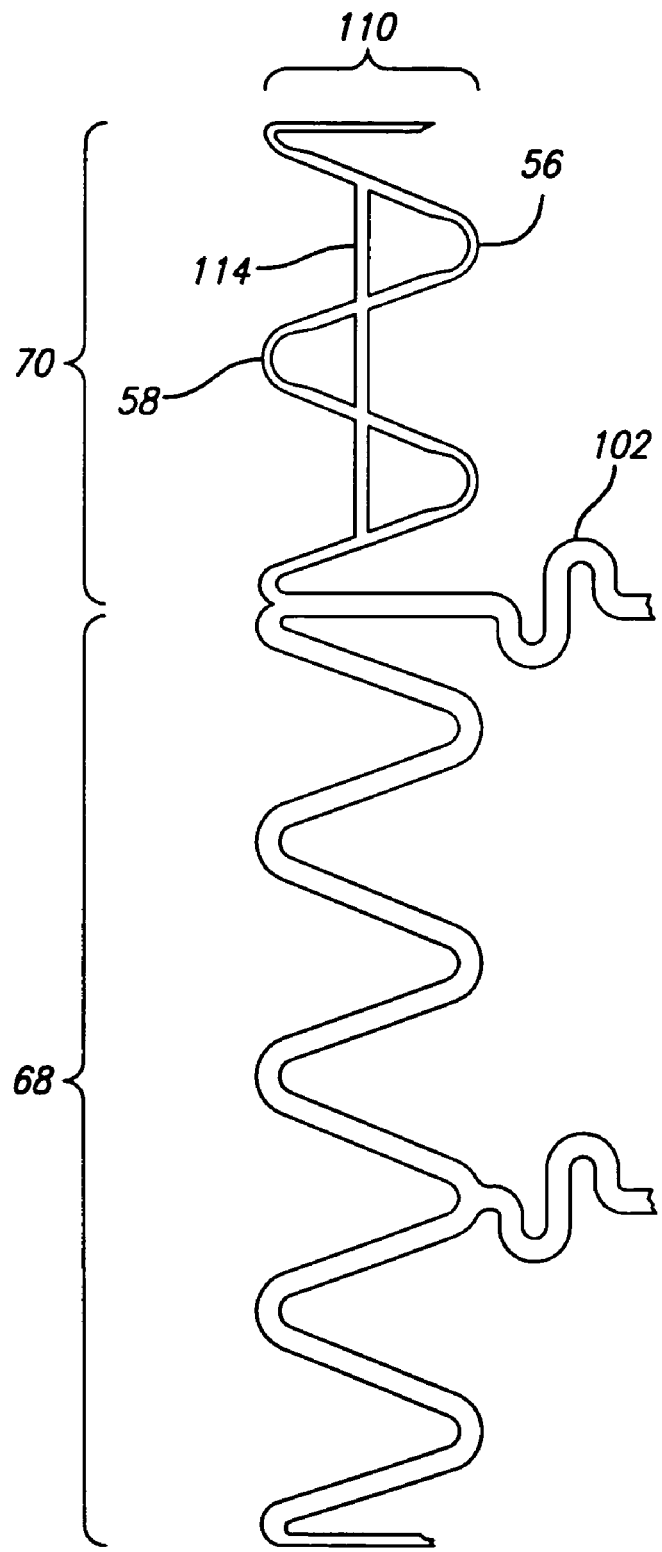
FIG. 20 is a plan view, depicting a single ring of the stent of FIG. 19 in an expanded condition.

When the stent 112 of FIG. 19 is deployed by expansion of the balloon 22, the first region 70 of the stent expands, with the reinforcing members 114 expanding therewith, prior to the expansion of the second region 68. As seen in FIG. 20 showing a single, expanded ring 110, the reinforcing members 114 expand until they are substantially straight, thus preventing further expansion of the first region 70 of the stent. By limiting expansion in the first region 70, the stent has struts in the first region 70 that maintain the undulating pattern. This is contrasted to the more expandable struts 66 in the first region 70 that tend to straighten out a bit more in the stent 10 depicted in the FIG. 10. Thus, the first region 70 of the stent provides increased vessel wall coverage in comparison to the embodiment depicted in FIG. 4.

As described above, the present invention staged expansion stent with anchors that embed into the arterial tissue at or outside the shoulder regions of a lipid pool during expansion can minimize the potential for plaque rupture due to high stresses within the fibrous cap. The anchors decouple luminal expansion from stent expansion within defined regions of the fibroatheroma.

Decoupling luminal expansion from stent expansion within defined regions of the fibroatheroma requires stent implantation to take place in, more precisely, three basic stages: (1) expansion of the arc between the stent anchors such that they span a distance greater than the arc spanned by the lipid pool; (2) initial expansion of the arc outside the stent anchors in order to embed the anchors into the arterial tissue; and (3) continued expansion of the arc outside the anchors in order to restore lumen patency. These three stages present a gross overview of the process and were discussed in general above.

The three stages can be further broken down into six different stages. FIGS. 21A-21F show, in cross-section, six stages of the expansion process.

Figure 21C:
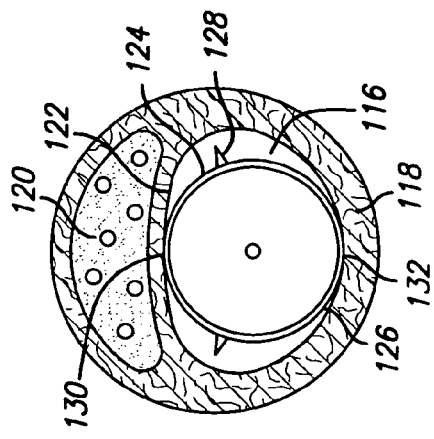
FIGS. 21A-21F show six phases of a stent expansion process.
Figure 21F:
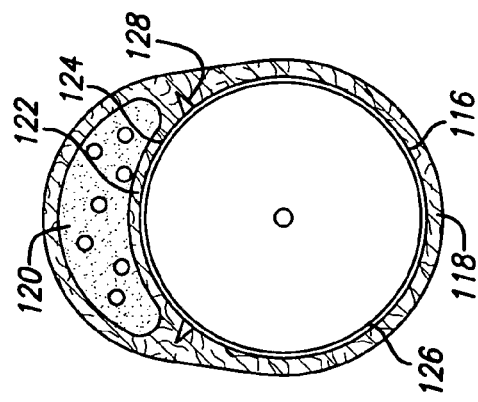
Figure 21B:
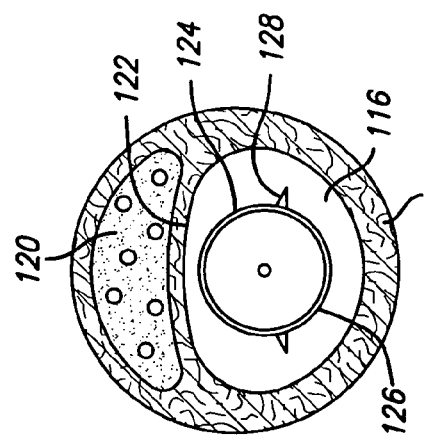
Figure 21E:
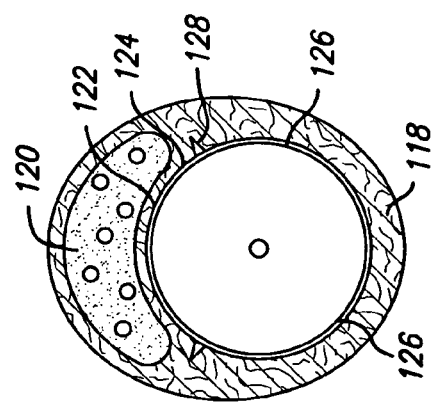
Figure 21A:
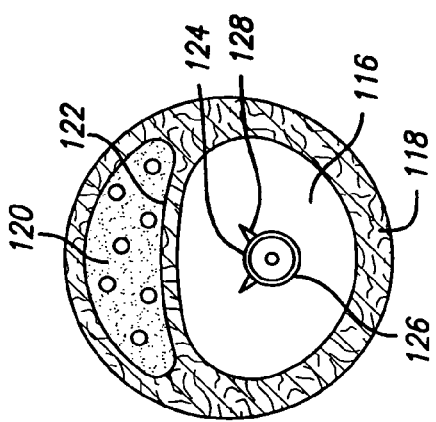

A cross-section of an artery with a vulnerable plaque is shown in FIG. 21A. The vessel contains a lumen 116 contained within vessel wall 118 and includes a large lipid pool 120 separated from the lumen 116 by a thin fibrous cap 122. The lumen 116 is not circular, but more oblong. The stent and delivery system in their crimped state are also shown in FIG. 21A. The stent includes a weak region 124 that expands very easily as compared to a strong region 126. These regions 124, 126 are separated by anchors 128. The anchors 128 in this embodiment in the unexpanded condition are spread apart by about 90 degrees.

FIG. 21B shows the first stage of deployment. Weak region 124 expands to its maximum or near maximum with relatively low balloon inflation pressure. This moves the anchors 128 farther apart circumferentially on the side adjacent to the lipid pool 120. Indeed, the anchors 128 have been spread to over 180 degrees apart. Minimal relative expansion occurs in strong region 126. The stent at this point is smaller than the lumen 116, so minimal wall contact force is generated. The lumen 116, lipid pool 120, fibrous cap 122, and vessel wall 118 are unchanged from that shown in FIG. 21A.

FIG. 21C shows further expansion until wall contact is first made at points 130 and 132. The arc length between the anchors 128 in weak region 124 is roughly equivalent to the same weak region 124 shown in FIG. 21B. This occurs because this region has already been maximally expanded. Although the arc length has not changed appreciably, the anchors 128 are now, in angular terms without considering diametrical change, less than about 180 degrees and more in the range of about 150 degrees apart as compared to FIG. 21B. The expansion to this stage has also occurred in strong region 126. At this moment, the contact force at points 130, 132 is minimal. Therefore, the lumen 116, lipid pool 120, fibrous cap 122, and vessel wall 118 are essentially unchanged from FIG. 21B. The anchors 128 have not yet punctured the vessel wall.

Figure 21D:
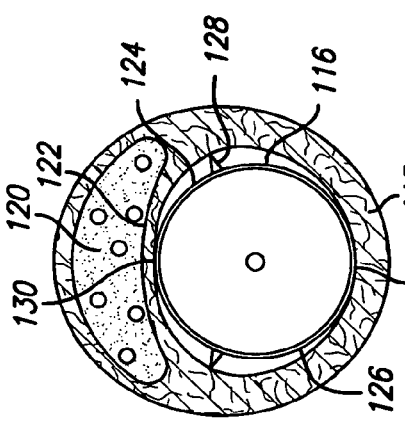

FIG. 21D shows the stent beginning to reshape the lumen 116 and the anchors 128 first penetrate the vessel wall 118. The arc length of weak region 124 is equivalent to that shown for the weak region 124 in FIG. 21C. Further expansion of the system occurs in strong region 126. The lumen 116 is reshaped to become less oblong and more circular than the lumen 116 shown in FIG. 21C. The lumen in FIG. 21D is reshaped but the vessel wall 118 is not stretched significantly. This means that minimal stress is placed on the vessel wall 118 and the fibrous cap 122. The vessel wall and fibrous cap thickness are also minimally affected, but their curvature has increased slightly. The vessel is beginning to assume a more oblong shape as well. The lipid pool 120 is also slightly more curved but is roughly the same area as the lipid pool 120 shown in FIG. 21C. The anchors 128 have initially penetrated the vessel wall near or just beyond the shoulders proximate to and on opposite sides of the fibrous cap 122.

FIG. 21E shows the lumen 116 becoming circular and anchors 128 fully penetrating the vessel wall 118. Further expansion of strong region 126 allows the stent to completely fill the lumen 116 and to mold to the circular shape of the balloon. The arc length of weak region 124 is equivalent to that of the weak region 124 shown in FIG. 21D. Since only a minimal amount of stress has been placed on the vessel wall 118 and fibrous cap 122, their thickness is relatively unchanged. The vessel has been forced into a more oblong shape because the lumen has become circular. The lipid pool area 120 is the same area as the lipid pool area shown in 21D, but its shape is more curved to fit into the oblong vessel near the circular lumen. The anchors 128 are fully penetrated into the vessel wall and protect the fibrous cap 122 from hoop stresses due to balloon expansion.

FIG. 21F shows further expansion of the stent with a protected fibrous cap 122. Strong region 126 continues expanding as the balloon pressure is increased and the lumen 116 expands to a larger diameter. Weak region 124 has an arc length equivalent to the weak region arc length shown in FIG. 21E. Anchors 128 are again situated about 90 degrees apart. The anchors 128 so deployed protect the fibrous cap 122 from hoop stresses during lumen expansion. The fibrous cap thickness is unchanged, but the cap follows the contour of the lumen. Since the fibrous cap 122 and lipid pool 120 are protected, the vessel wall 118 and the strong region 126 stretch and become thinner compared to the vessel wall 118 shown in FIG. 21E. The lipid pool 120 again has an equivalent area to the lipid pool shown in FIG. 21E, but its shape is altered slightly. The vessel becomes somewhat egg shaped during this lumen expansion stage. After balloon deflation, the stent and anchors remain within the vessel to prevent the fibrous cap from rupturing.

The morphological changes in the tissue that are induced by the expanding stent illustrated in FIG. 21D are of particular importance. Moderate levels of luminal reshaping occur as the anchors come into contact with the luminal surface and begin to penetrate the tissue during this stage of the expansion process. Empirical studies suggest that the luminal reshaping that occurs in the early stages of the stent deployment process can elevate the stresses within the fibrous plaque cap to a magnitude that is in the range of published data on the rupture stress of non-ulcerated plaque caps. (Lendon, et al., J Biomed Eng 1993, Vol. 15, pp. 27-33.) However, the bulk luminal expansion that occurs in the late stages of stent deployment can raise the magnitude of the stress within the shoulder region of the fibrous plaque cap to levels that are significantly greater than this rupture value. (C. Feezor, D. Kilpatrick, J. Ellis, "Acute Mechanical Response of Human Coronary Fibroatheromas to Stenting," 2003 Summer Bioengineering Conference, June 25-29, pp. 167-68 (Key Biscayne, Fla. 2003).)

The nature of the present invention stent, in various embodiments, is such that the shoulder regions of the fibrous plaque cap are decoupled from the bulk luminal expansion that can dramatically increase the magnitude of the stresses beyond the rupture value. The luminal reshaping that takes place prior to anchoring of the stent as shown in FIG. 21D of the deployment process should be sufficiently low to minimize the elevation of the stresses within the shoulder region of the fibrous cap to below rupture values. Maximum lumen circularity is obtained at about the same point at which the maximum stress begins to rise in the shoulder region. The present invention stent therefore minimizes the potential of inadvertent rupture of the fibrous plaque cap.

A stent having a weak first region and a strong second region may be part of a dilatation system that is removed after the dilatation procedure. For example, in an alternative embodiment, the stent is made from a superelastic material, such as a nickel-titanium (i.e., nitinol) alloy, with its shape memory set in the smaller, crimped, delivery profile. The nitinol stent is thus self-contracting. The stent is mounted onto a balloon with the contraction forces of the stent maintaining the stent on the balloon, although the stent may additionally be bonded to the balloon. As the balloon is inflated and the stent is expanded during a dilatation procedure, the stent redistributes the expansion forces of the balloon so that the stent expands in stages with the weak first region of the stent expanding first, followed by expansion of the strong second region. The self-contracting forces of the stent aid in squeezing the balloon down to a small profile during deflation of the balloon. The stent and catheter are then withdrawn from the patient.

During delivery, the nitinol stent is in the austenitic phase, and upon expansion at the lesion, it transitions into the martensitic phase. Specifically, during the dilation procedure, the stent remains mostly in the stress-induced martensitic (SIM) phase as radially outward expansion forces from the inflating balloon engage the stent. As the balloon is deflated, the outward stress on the stent is removed and the stent returns generally to its smaller diameter austenitic phase. The inherent superelasticity of the nitinol alloy exerts gentler forces on the fibrous cap further minimizing the potential for rupture.

In other alternative embodiments, any portion of the disclosed stents can be made from a metal alloy or from a polymer. For example, the rings can be made from a metal alloy while the connecting links can be made from a metal alloy or a polymer. Typically, if the links are made from a polymer, the stent will be more longitudinally flexible than if the links were made from a metal alloy. Also, the anchors can be made from either a metal alloy or a polymer.

Exemplary of the metallic material used in forming the rings, links and anchors of the stent are stainless steel, titanium, nickel-titanium, tantalum, gold, cobalt-chromium, platinum, palladium, iridium, or any combination or alloys thereof. Other metals, metal alloys and polymers may also be used to form the present invention stent.

The rings and links are optionally configured so that the metallic surface area (metal-to-artery ratio) is preferably less than about 20%, and more preferably is between about 20% and 10%, thus providing good scaffolding and providing a more cylindrical lumen.

Exemplary of the biocompatible polymer material used in forming the rings, the links or the anchors includes the group of polymers consisting of polyurethanes, polyetherurethanes, polyesterurethanes, silicone, thermoplastic elastomer (C-flex), polyether-amide thermoplastic elastomer (Pebax), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (Kraton) and polyester thermoplastic elastomer (Hytrel), polyethylene, polylactic acid (PLA), polyglycolic acid (PGA), and polylactic-co-glycolic acid (PLGA).

The present invention stent may also be used in connection with a drug or therapeutic agent to perform a variety of functions, from preventing blood clots to promoting healing. Further, it is well known that the stent (when made from a metal) may require a primer material coating such as a polymer to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent.

Figure 15:
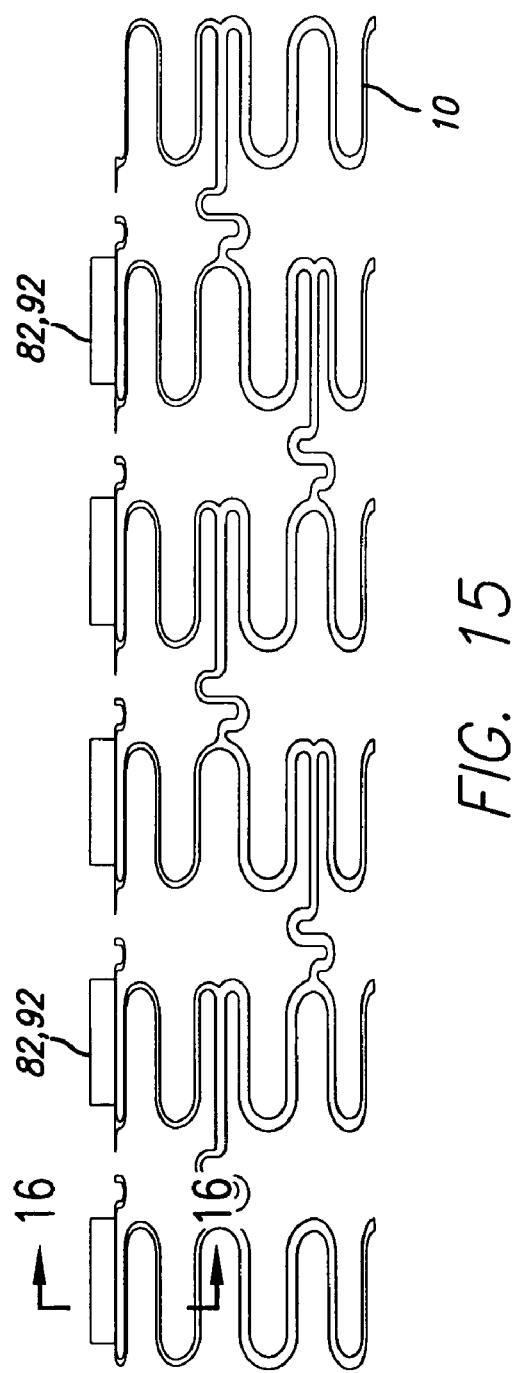
FIG. 15 is a side elevational view of a stent in an unexpanded condition having anchors on selected portions.
Figure 16:
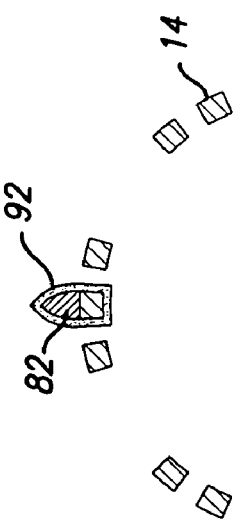
FIG. 16 is a cross-sectional view taken along line 16-16 in FIG. 15 depicting the anchor on a portion of the stent.

As an example and as shown in FIGS. 15 and 16, an active agent coating 92 on the rings, links and/or anchors can inhibit the activity of endothelial cells. Similarly, an active agent coating on selective rings 40, links and/or anchors can also inhibit the activity of smooth muscle cells. More specifically, the active agent is aimed at inhibiting abnormal or inappropriate migration and proliferation of smooth muscle cells. The active agent can also include any substance capable of exerting a therapeutic or prophylactic effect in the practice of the present invention. The agent can also be for enhancing wound healing in a vascular site or improving the structural and elastic properties of the vascular site. The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of therapeutic agents or drugs that are suitable for use with the polymeric materials include sirolimus, everolimus, actinomycin D (ActD), taxol, paclitaxel, or derivatives and analogs thereof. Examples of agents include other antiproliferative substances as well as antineoplastic, anti-inflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents that can be combined with the polymeric materials include antiplatelets, anticoagulants, antifibrins, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, Adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as platelet-derived growth factor (PDGF) receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents is known in the art. Furthermore, the calculation of dosages, dosage rates and appropriate duration of treatment are previously known in the art.

Representative examples of polymers that can be used to coat a stent in accordance with the present invention include ethylene vinyl alcohol copolymer (commonly known by the generic name EVOH or by the trade name EVAL), poly (hydroxyvalerate); poly(L-lactic acid); polycaprolactone; poly(lactide-co-glycolide); poly(hydroxybutyrate); poly(glycolic acid); poly(hydroxybutyrate-co-valerate); polydioxanone; polyorthoester; polyanhydride, poly(D,L-lactic acid); poly(glycolicacid-co-trimethylene carbonate); polyphosphoester; polyphosphoester urethane; poly(amino acids); cyanoacrylates; poly(trimethylene carbonate); poly (iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; polybutylmethacrylate; rayon; rayon-triacetate; poly(glycerol-sebacate); cellulose acetate; cellulose butyrate; cellulose acetate butyrate; cellophane; cellulose nitrate; cellulose propionate; cellulose ethers; and carboxymethyl cellulose.

"Solvent" is a liquid substance or composition that is compatible with the polymer and is capable of dissolving the polymer at the concentration desired in the composition. Representative examples of solvents include chloroform, acetone, water (buffered saline), dimethylsulfoxide (DMSO), propylene glycol methyl ether (PM,) iso-propylalcohol (IPA), n-propylalcohol, methanol, ethanol, tetrahydrofuran (THF), dimethylformamide (DMF), dimethyl acetamide (DMAC), benzene, toluene, xylene, hexane, cyclohexane, heptane, octane, pentane, nonane, decane, decalin, ethyl acetate, butyl acetate, isobutyl acetate, iso-propyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof. Therapeutic substance contained in the coating can be for inhibiting the activity of vascular smooth muscle cells. More specifically, therapeutic substance can be aimed at inhibiting abnormal or inappropriate migration and/or proliferation of smooth muscle cells for the inhibition of restenosis. Therapeutic substance can also include any active agent capable of exerting a therapeutic or prophylactic effect in the practice of the present invention. For example, therapeutic substance can be for enhancing wound healing in a vascular site or improving the structural and elastic properties of the vascular site.

The stent of the present invention can be made in many ways. One method of making the stent is to cut a thin-walled tube, from stainless steel tubing for example, to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

After laser cuffing the stent pattern, the stent is preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. Other electropolishing solutions are well known in the art. The stent may be further treated if desired, for example by applying a biocompatible coating such as described above.

Other methods of forming the stent of the present invention can be used, such as chemical etching; electric discharge machining; laser cutting a flat sheet and rolling it into a cylinder, and the like, all of which are well known in the art at this time.

The anchors may be made of the same material as the stent, such as stainless steel. In one embodiment, the anchors and the stent may be made from the same piece of material. In other embodiments, the anchors are coupled to the stent by adhesive bonding, laser bonding or fusion, or other methods well known in the art. In embodiments wherein the anchors are coupled to the stent, the anchors and the stent may be made from different materials. For example, the stent may be made of stainless steel and the anchors may be made of nickel-titanium.

While the invention has been illustrated and described herein in terms of its use as an intravascular stent, it will be apparent to those skilled in the art that the stent can be used in other body lumens. Other modifications and improvements may be made without departing from the scope of the invention.

We claim:

1. An intravascular stent, comprising:
   a plurality of rings having struts and aligned along a common longitudinal axis to define a tube having a circumference;
   a link substantially parallel to the longitudinal axis and interconnecting adjacent rings;
   a first region spanning an arc along the circumference and axially along the length of the stent;
   a second region, excluding the first region, spanning the circumference and axially along the length of the stent, wherein the struts in the first region are structurally weaker than the struts in the second region; and
   at least one radially outwardly extending anchor disposed on the link along the circumference such that every anchor is at a transition between the first region and the second region.

2. The stent of claim 1, wherein the at least one anchor extends lengthwise substantially along a length of the link and includes a wedge-shaped cross-section.

3. The stent of claim 1, wherein the stent further comprises a plurality of anchors that are aligned lengthwise parallel to the longitudinal axis of the stent and a gap is located lengthwise between adjacent anchors.

4. The stent of claim 1, wherein the at least one anchor is coated with a therapeutic agent.

5. The stent of claim 1, wherein the link includes an undulating portion along a length thereof.

6. The stent of claim 1, wherein the stent further comprises at least two radially outwardly extending anchors each disposed along the circumference at a respective transition between the first region and the second region, and wherein when the stent is inflated, the anchors are embedded in opposite shoulders of a lipid pool in a patient's vessel.

7. The stent of claim 1, wherein the struts in the first region include undulations with peaks and valleys, and reinforcing members with peaks and valleys that subtend the peaks of the struts.

8. The stent of claim 1, wherein the rings include a first material, and the anchors include a second material that is more flexible than the first material.

9. The stent of claim 8, wherein the second material includes a superelastic nickel-titanium alloy.

10. The stent of claim 1, the stent includes a nickel-titanium alloy that is self-contracting through a phase change in the alloy.

11. The stent of claim 1, wherein the at least one anchor includes a cutting edge.

12. The stent of claim 1, wherein the stent when expanded includes an asymmetrical circular cross-sectional shape wherein the first region is less arcuate than the second region.

13. The stent of claim 1, wherein at least a portion of the stent includes a coating of a drug or therapeutic agent.

14. A balloon expandable intravascular stent for use in a body lumen, comprising:
a plurality of rings, each ring having struts, aligned along a common longitudinal axis of the stent and defining a stent circumference;
a first region spanning a first angular distance along the stent circumference;
a second region spanning a second angular distance along the stent circumference excluding the first angular distance, the struts in the first region being relatively smaller than the struts in the second region;
a first transition at a first interface between the first region and the second region,
the first transition extending the length of the stent along a line which is substantially parallel to the longitudinal axis of the stent;
a second transition at a second interface between the first region and the second region, the second transition extending the length of the stent along a line which is substantially parallel to the longitudinal axis of the stent;
a first series of links interconnecting each pair of adjacent rings, the links of the first series positioned substantially along the first transition and aligned linearly;
a second series of links interconnecting each pair of adjacent rings, the links of the second series positioned substantially along the second transition and aligned linearly;
at least one anchor positioned such that every anchor is on an outer surface of the first series of links and aligned with the links of the first series; and
at least one anchor positioned such that every anchor is on an outer surface of the second series of links and aligned with the links of the second series.

15. The stent of claim 14, further comprising a plurality of links interconnecting adjacent rings and not disposed at the first and second transitions.

16. The stent of claim 14, wherein at least one of the links of the first series includes an undulating portion, and at least one of the links of the second series includes an undulating portion.

17. A method of providing a stent, comprising:
aligning a plurality of rings along a common longitudinal axis of the stent and defining a stent circumference, wherein each ring includes struts;
defining a first region spanning a first angular distance along the circumference of the stent;
defining a second region spanning a second angular distance along the circumference of the stent excluding the first angular distance, wherein the struts of the first region are relatively weaker than the struts of the second region;
defining a first transition between the first region and the second region, the first transition extending the length of the stent along a line substantially parallel to the longitudinal axis of the stent;
defining a second transition between the first region and the second region, the second transition extending the length of the stent along a line substantially parallel to the longitudinal axis of the stent;
interconnecting a pair of adjacent rings with a first link, the first link being positioned substantially along the first transition;
interconnecting a pair of adjacent rings with a second link, the second link being positioned substantially along the second transition;
providing at least one anchor on an outer surface of at least one of the first and second links;
positioning the stent in a target area including the vulnerable plaque;
aligning the first region of the stent to substantially overly the vulnerable plaque;
expanding the first region until substantially fully deployed and the at least one anchor is embedded into the vessel wall proximate to and on opposite sides of the vulnerable plaque; and
expanding the second region of the stent until the second region of the stent is fully deployed.

18. The method of claim 17, wherein the stent includes a superelastic nickel-titanium alloy wherein the stent is shape set to have a smaller diameter in the austenitic phase and is expanded to a larger diameter in the martensitic phase.

19. The method of claim 17, wherein during expansion of the first region, the anchors are spread apart by greater than about 180 degrees.

20. An intravascular stent for use in a body lumen, comprising:
a plurality of rings, each ring having struts and being aligned along a common longitudinal axis of the stent and defining a stent circumference;
a first region spanning a first angular distance along the circumference of the stent;
a second region spanning a second angular distance along the circumference of the stent excluding the first angular distance, the struts of the first region being relatively weaker than the struts of the second region;
a first transition between the first region of the circumference of the stent and the second region of the circumference of the stent, the first transition extending the length of the stent along a line substantially parallel to the longitudinal axis of the stent;
a second transition between the first region of the circumference of the stent and the second region of the circumference of the stent, the second transition extending the length of the stent along a line which is substantially parallel to the longitudinal axis of the stent;

a first link interconnecting each pair of adjacent rings along the length of the stent,
the first link positioned substantially along the first transition;
a second link interconnecting each pair of adjacent rings along the length of the stent, the second link positioned substantially along the second transition;
at least one anchor positioned on an outer surface of the first link; and
at least one anchor positioned on an outer surface of the second link.

* * * * *